United States Patent

Clemence et al.

[11] Patent Number: 5,817,674
[45] Date of Patent: *Oct. 6, 1998

[54] QUINOLINE COMPOUNDS

[75] Inventors: Francois Clemence; Michel Fortin, both of Paris; Jean-Luc Haesslein, Courtry, all of France

[73] Assignee: Roussel Uclaf, France

[*] Notice: The term of this patent shall not extend beyond the expiration date of Pat. No. 5,324,839.

[21] Appl. No.: 583,637

[22] Filed: Jan. 5, 1996

Related U.S. Application Data

[63] Continuation of Ser. No. 191,862, Feb. 4, 1994, abandoned, which is a continuation of Ser. No. 832,749, Feb. 7, 1992, abandoned.

[30] Foreign Application Priority Data

Feb. 7, 1991 [FR] France ................................ 91 10435
Aug. 20, 1991 [FR] France ................................ 91 01374

[51] Int. Cl.$^6$ .................................................. A61K 31/395
[52] U.S. Cl. ........................ 514/311; 514/253; 514/312; 514/314; 544/128; 544/235; 544/237; 544/238; 544/283; 544/285; 544/349; 544/363; 546/141; 546/149; 546/153; 546/156; 546/168; 546/174; 546/180
[58] Field of Search ................................ 514/312, 311, 514/174; 546/153, 152, 168

[56] References Cited

U.S. PATENT DOCUMENTS

| | | | |
|---|---|---|---|
| 4,444,584 | 4/1984 | Serban et al. | 546/153 |
| 4,642,347 | 2/1987 | Kreft, III et al. | 546/181 |
| 4,904,786 | 2/1990 | Musser et al. | 546/152 |
| 4,918,081 | 4/1990 | Huang et al. | 546/153 |
| 4,920,131 | 4/1990 | Huang et al. | 546/153 |
| 4,920,132 | 4/1990 | Huang et al. | 546/153 |
| 4,920,133 | 4/1990 | Huang et al. | 546/153 |
| 4,968,701 | 11/1990 | Ackerman et al. | 514/312 |
| 5,081,126 | 1/1992 | Oku et al. | 514/312 |
| 5,093,340 | 3/1992 | Mohrs et al. | 514/312 |
| 5,093,346 | 3/1992 | Carini et al. | 514/326 |
| 5,157,040 | 10/1992 | Greenlee et al. | 514/312 |
| 5,324,839 | 6/1994 | Clemence et al. | 514/311 |
| 5,444,071 | 8/1995 | Roberts et al. | 514/312 |
| 5,478,938 | 12/1995 | Clemence et al. | 544/238 |
| 5,591,762 | 1/1997 | Havel | 546/152 |
| 5,650,415 | 7/1997 | Tang | 546/153 |

FOREIGN PATENT DOCUMENTS 412848  2/1991  European Pat. Off. .

Primary Examiner—Donald G. Daus
Attorney, Agent, or Firm—Bierman, Muserlian and Lucas

[57] ABSTRACT

Compounds of the formula

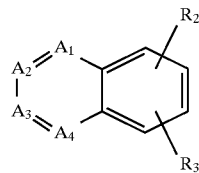

in all possible racemic, enantiomeric and diastereoisomeric forms and their non-toxic, pharmaceutically acceptable salts with acids and bases having antagonistic properties for angiotensin II receptors and a process and novel intermediates for their properties.

8 Claims, No Drawings

QUINOLINE COMPOUNDS

PRIOR APPLICATIONS

This application is a continuation of U.S. patent application Ser. No. 191,862 filed Feb. 4, 1994 which is a continuation of U.S. patent application Ser. No. 832,749 filed Feb. 7, 1992, both now abandoned.

OBJECTS OF THE INVENTION

It is an object of the invention to provide the novel compounds of formula $I_B$ and their non-toxic, pharmaceutically acceptable salts with acids and bases.

It is another object of the invention to provide novel compositions and a method of inhibiting the effects of angiotensin II.

These and other objects and advantages of the invention will become obvious from the following detailed description.

THE INVENTION

The novel compounds of the invention are selected from the group consisting of all possible racemic, enantiomeric and diastereoisomeric forms of a compound of the formula

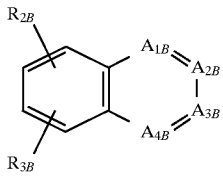

$I_B$ wherein $R_{2B}$ and $R_{3B}$ are individually selected from the group consisting of a) hydrogen, halogen, hydroxy, mercapto, cyano, nitro, sulfo, formyl, benzoyl, acyl of up to 12 carbon atoms, free, salified or esterified carboxy, cycloalkyl of 3 to 7 carbon atoms, acyloxy of up to 12 carbon atoms, b) alkyl, alkenyl, alkynyl, alkoxy and alkylthio of up to 6 carbon atoms and optionally substituted, c) aryl, aralkyl, aralkenyl, aryloxy and arylthio of up to 6 alkyl and alkenyl carbon atoms, the aryl being a monocyclic of 5 or 6 ring members or condensed rings of 8 to 10 ring members optionally containing at least one heteroatom chosen from oxygen, nitrogen and sulfur, and optionally substituted,

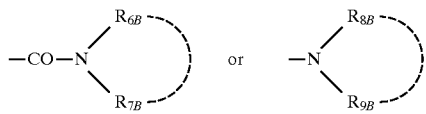

d)

either $R_{6B}$ and $R_{7B}$ or $R_8$ and $R_{9B}$ are individually selected from the group consisting of hydrogen, alkyl or alkenyl of up to 6 carbon atoms and optionally substituted by at least one member of the group consisting of halogen, hydroxy, alkyl or alkenyl of 2 to 6 carbon atoms substituted by alkoxy of 1 to 6 carbon atoms, aryl or aralkyl of 1 to 6 alkyl carbon atoms, the aryl being a monocyclic of 5 or 6 ring members or condensed rings of 8 to 10 ring members optionally containing at least one heteroatom chosen from oxygen, nitrogen and sulfur and optionally substituted by at least one member of the group consisting of halogen, hydroxy, cyano, trifluoromethyl, nitro, alkyl, alkenyl, alkoxy, alkylthio and acyl of up to 6 carbon atoms, free, salified or esterified carboxy, $—(CH_2)_{m1}—S(O)_{m2}—X—R_{14}$, $m_1$ is an integer from 0 to 4 and $m_2$ is an integer from 0 to 2, and either $—X—R_{14}$ is $—NH_2$ or X is selected from the group consisting of —NH—, —NH—CO—, —NH—CO—NH— and a single bond and $R_{14}$ is alkyl, alkenyl or aryl optionally substituted, or $R_{6B}$ and $R_{7B}$ or $R_{8B}$ and $R_{9B}$ form respectively with the nitrogen atom to which they are attached a monocycle of 5 or 6 ring members or condensed rings of 8 to 10 ring members optionally containing one or more heteroatoms chosen from oxygen, nitrogen and sulfur, and optionally substituted by at least one member of the group consisting of halogen, hydroxy, cyano, trifluoromethyl, nitro, alkyl, alkenyl, alkoxy, alkylthio and acyl of up to 6 carbon atoms, free, salified or esterified carboxy, or $R_{8B}$ and $R_{9B}$ are individually acyl of a carboxylic acid of up to 6 carbon atoms, e) $—(CH_2)_{m1}—S(O)_{m2}—X—R_{14}$ as defined above, $A_{1B}$, $A_{2B}$, $A_{3B}$ and $A_{4B}$ are individually nitrogen or $=C—R_{4B}$, either $R_{4B}$ is $R_1$ such that $R_1$ is selected from the group consisting of a) hydrogen, hydroxyl, mercapto, nitro, cyano, benzoyl, acyl of up to 12 carbon atoms, free, salified or esterified carboxy, cycloalkyl of 3 to 7 carbon atoms, b) alkyl, alkenyl, alkynyl, alkoxy and alkylthio of up to 6 carbon atoms and optionally substituted, c) aryl, aralkyl, aralkenyl, aryloxy and arylthio of up to 6 alkyl and alkenyl carbon atoms, the aryl being a monocycle of 5 or 6 ring members or condensed rings of 8 to 10 ring members optionally containing one or more heteroatoms chosen from oxygen, nitrogen and sulfur, and optionally substituted, or $R_{4B}$ is $—R_5—Y_B$ such that:

$R_5$ is selected from the group consisting of a) divalent alkylene of up to 4 carbon atoms and optionally substituted by at least one halogen, oxo and —OZ, Z is hydrogen or alkyl of 1 to 4 carbon atoms optionally substituted by an amino acid, b) —NH—, $—O(CH_2)_n$ or $—S(CH_2)_n—$, n is an integer from 0 to 4, $Y_B$ is $—Y_{1B}—B—Y_{2B}$ in which :

$Y_{1B}$ is a monocyclic aryl of 5 or 6 ring members or condensed rings of 8 to 10 ring members optionally containing one or more heteroatoms chosen from oxygen, nitrogen and sulfur, and optionally substituted by one of $R_{2B}$ or $R_{3B}$, B is either a single bond between $Y_{1B}$ and $Y_{2B}$ or is selected from the group consisting of: —CO—, —CO—NH—, —NH—CO—, —NH—$(CH_2)_n$—, —O—$(CH_2)_n$— and —S—$(CH_2)_n$—, n is 0 to 4, $Y_{2B}$ is, if B is a single bond, selected from the group consisting of hydrogen, halogen, hydroxyl, cyano, nitro, trifluoromethyl, free, salified or esterified carboxy, tetrazole and isoxazole, or, whatever the value of B and $Y_{2B}$ is one of the values for $Y_{1B}$, it being understood that:

1) the products of formula $I_B$ are such that at least one and at most two of $A_{1B}$, $A_{2B}$, $A_{3B}$ and $A_{4B}$ is nitrogen and at least one is methine substituted by $—R_5—Y_B$, as defined above, it being known that if one of $A_{1B}$, $A_{2B}$, $A_{3B}$, $A_{4B}$ is methine substituted by a benzyl, then another of $A_{1B}$, $A_{2B}$, $A_{3B}$, $A_{4B}$ is $—R_5—Y_B$, $Y_B$ is $Y_{1B}—B—Y_{2B}$ in which $Y_{2B}$ has the values for $Y_{1B}$; 2) the products of formula $I_B$ cannot be the following products:

either one of $R_{2B}$ and $R_{3B}$ is methyl or methoxy, $A_{1B}$ is methine substituted by benzyl, $A_{2B}$ and $A_{4B}$ are nitrogen and $A_{3B}$ is methine substituted by phenyl or $R_{2B}$ and $R_{3B}$ are hydrogen or methyl and $A_{1B}$, $A_{2B}$, $A_{3B}$ and $A_{4B}$ are such that: two are methine substituted by benzyl, one is nitrogen, and the last one is nitrogen atom or methine or $A_{1B}$ is methine, $A_{2B}$ is methine substituted by methyl substituted by hydroxyl or acetyl, $A_{3B}$ is nitrogen, $R_{2B}$ and $R_{3B}$ in position 6 and 7 are alkoxy of up to 3 carbon atoms and $A_{4B}$ is methine substituted by —$(CH_2)_n$—Ar, n is an integer from 0 to 2 and Ar is aromatic, or $A_{1B}$ is nitrogen, $A_{2B}$ is

$R_{4B}$ is hydrogen, alkyl substituted by at least one fluorine or cycloalkyl or hydroxyl, alkoxy of 1 to 4 carbon atoms or phenyl, cycloalkyl or phenyl.
$A_{3B}$ is

$R_{4B}$ is hydrogen, alkyl, cycloalkyl, free, esterified or salified carboxy, cyano, nitro, phenyl or phenylalkyl,
$A_{4B}$ is

$R_{4B}$ is —$R_5$—$Y_B$, $R_5$ is —$O(CH_2)_n$—, n is 1, $Y_B$ is $Y_{1B}$—B—$Y_{2B}$ in which:

either $Y_{1B}$ is phenylene optionally substituted by a member of the group consisting of alkyl, alkoxy, halogen, trifluoromethyl, cyano and nitro, B is a single bond and $Y_{2B}$ is phenyl carrying a substituent chosen from the group consisting of: tetrazolyl, —CONH tetrazolyl, optionally esterified carboxy, —$CONHSO_2Rd$, Rd is an optionally substituted alkyl, cycloalkyl or phenyl and optionally carrying another substituent chosen from alkyl, alkoxy, halogen, trifluoromethyl, cyano and nitro, or B is a single bond, $Y_{2B}$ is hydrogen, and $Y_{1B}$ has the values indicated above for $Y_{2B}$, $R_{2B}$ and $R_{3B}$ are selected from the group consisting of halogen; hydroxyl; trifluoromethyl; cyano; nitro; alkyl of 1 to 4 carbon atoms optionally substituted by amino or mono or dialkylamino of 3 to 8 carbon atoms, hydroxyl, or alkoxy of 1 to 4 carbon atoms; alkoxy of 1 to 4 carbon atoms optionally substituted by a member of the group consisting of fluorine; alkylthio of 1 to 6 carbon atoms; amino and carbamoyl optionally substituted by one or two alkyl to contain respectively at most 6 and 7 carbon atoms; carboxy; alkoxycarbonyl of 1 to 4 carbon atoms; acyl of 1 to 4 carbon atoms.

3) 4-[[(2-butyl-4-quinolinyl)-oxy]-methyl]benzoic acid hydrochloride,
Methyl 4'-[[(2-butyl-4-quinolinyl)-oxy](1,1'-biphenyl)-2-carboxylate,
Methyl 4'-[[(3-butyl-5-methylthio-4-quinolinyl)-oxy]-methyl](1,1'-biphenyl)-2-carboxylate,
Diethylamine salt of 4'-[[(3-butyl-1,4-dihydro-5-(methylthio)-4-quinolinyl)-oxy]-methyl](1,1'-biphenyl)-2-carboxylic acid and
4-[[(3-butyl-4-quinolinyl)-oxy]-methyl](1,1'-biphenyl)-2-carboxylic acid, and their non-toxic, pharmaceutically acceptable addition salts with mineral and organic acids and mineral and organic bases.

A preferred group of compounds are those of the formula

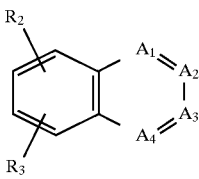

I in which: $R_2$ and $R_3$ are individually selected from the group consisting of:
a) hydrogen, halogen, hydroxyl, mercapto, cyano, nitro, sulfo, formyl, benzoyl, acyl of up to 12 carbon atoms, free, salified or esterified carboxy, cycloalkyl of 3 to 7 carbon atoms,
b) alkyl, alkenyl, alkynyl, alkoxy and alkylthio of up 6 carbon atoms and optionally substituted,
c) aryl, aralkyl, aralkenyl, aryloxy and arylthio of up 6 alkyl and alkenyl carbon atoms, the aryl being a monocycle of 5 or 6 ring members or condensed rings of 8 to 10 optionally containing one or more heteroatoms chosen from oxygen, nitrogen and sulfur, and optionally substituted,

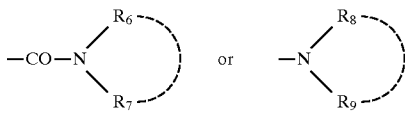

d)

in which:
either $R_6$ and $R_7$ or $R_8$ and $R_9$ are individually selected from the group consisting of: hydrogen, alkyl or alkenyl of up 6 carbon atoms and optionally substituted by at least one member of the group consisting of halogen, hydroxyl, alkyl or alkenyl of 2 to 6 carbon atoms substituted by alkoxy of 1 to 6 carbon atoms, aryl and aralkyl of 1 to 6 alkyl carbon atoms, the aryl being monocycle of 5 or 6 ring members or condensed rings of 8 to 10 ring members optionally containing one or more heteroatoms chosen from oxygen, nitrogen, and sulfur, and optionally substituted by at least one member of the group consisting of halogen, hydroxy, cyano, trifluoromethyl, nitro, alkyl, alkenyl, alkoxy, alkylthio and acyl of up to 6 carbon atoms, free, salified or esterified carboxy, or $R_6$ and $R_7$ or $R_8$ and $R_9$ form respectively with the nitrogen atom to which they are attached a monocycle of 5 or 6 ring members or condensed rings of 8 to 10 ring members optionally containing one or more heteroatoms chosen from oxygen, nitrogen and sulfur, and optionally substituted by at least one member of the group consisting of halogen, hydroxy, cyano, trifluoromethyl, nitro, alkyl, alkenyl, alkoxy, alkylthio and acyl of up to 6 carbon atoms, free, salified or esterified carboxy, or $R_8$ and $R_9$ individually are acyl of a carboxylic acid of up to 6 carbon atoms, $A_1$, $A_2$, $A_3$ and $A_4$ are individually nitrogen or

such that:
either $R_4$ is $R_1$ such that $R_1$ is selected from the group consisting of: a) hydrogen, hydroxyl, mercapto, cyano, benzoyl, acyl of up to 12 carbon atoms, free, salified or esterified carboxy, cycloalkyl of 3 to 7 carbon atoms, b) alkyl, alkenyl, alkynyl, alkoxy and alkylthio of up to 6 carbon atoms and optionally substituted, c) aryl, aralkyl, aralkenyl, aryloxy and arylthio of up to 6 alkyl and alkenyl carbon atoms, the aryl being a monocycle of 5 or 6 ring members or condensed rings of 8 to 10 ring members optionally containing one or more heteroatoms chosen from oxygen, nitrogen and sulfur, and optionally substituted, or $R_4$ is —$R_5$—Y such that:

$R_5$ is selected from the group consisting of: a) divalent alkylene of up to 4 carbon atoms and optionally substituted by at least one of halogen, oxo and —OZ, Z is hydrogen or alkyl of 1 to 4 carbon atoms optionally substituted by an amino acid, b) —NH—, —O(CH$_2$)$_n$— or —S(CH$_2$)$_n$—, n is an integer from 0 to 4, Y is —Y$_1$—B—Y$_2$— in which:

$Y_1$ is a monocycle aryl of 5 or 6 ring members or condensed rings of 8 to 10 ring members optionally containing one or more heteroatoms chosen from oxygen, nitrogen and sulfur, and optionally substituted by at least one or more of $R_2$ or $R_3$, B is either a single bond between $Y_1$ and $Y_2$, or is selected from the group consisting of —CO—, —CO—NH—, —NH—CO—, —NH—(CH$_2$)$_n$—, —O—(CH$_2$)$_n$— and —S—(CH$_2$)$_n$—, n is 0 to 4, $Y_2$ is, if B is a single bond, selected from the group consisting of hydrogen, halogen, hydroxyl, cyano, nitro, trifluoromethyl, free, salified or esterified carboxy, tetrazole or isoxazole, or, whatever the value of B and $Y_2$ has a value of $Y_1$, it being understood that:

1) the products of formula I are such that at least one and at most two of $A_1$, $A_2$, $A_3$ and $A_4$ is nitrogen and at least one is methine substituted by —$R_5$Y, Y is —Y$_1$—B—Y$_2$, $Y_2$ is from the values of $Y_1$, it being known that if one of $A_1$, $A_2$, $A_3$, $A_4$ is methine substituted by benzyl, then another of $A_1$, $A_2$, $A_3$, $A_4$ is —$R_5$—Y;

2) the products of formula I cannot be the following products:

either one of $R_2$ and $R_3$ is methyl or methoxy, $A_1$ is methine substituted by benzyl, $A_2$ and $A_4$ are nitrogen and $A_3$ is methine substituted by phenyl, or $R_2$ and $R_3$ are hydrogen or methyl and $A_1$, $A_2$, $A_3$ and $A_4$ are such that: two are methine substituted by benzyl, one is nitrogen, and the last one is nitrogen or methine, or $A_1$ is methine, $A_2$ is methine substituted by methyl substituted by hydroxyl or acetyl, $A_3$ is nitrogen, $R_2$ and $R_3$ in position 6 and 7 both are alkoxy of 1 to 3 carbon atoms and $A_4$ is methine substituted by —(CH$_2$)$_n$—Ar, n is an integer form 0 to 2 and Ar is aromatic, or $A_1$ is nitrogen, $A_2$ is

$R_4$ is hydrogen, alkyl optionally substituted by one or more fluorine or cycloalkyl, hydroxyl, alkoxy of 1 to 4 carbon atoms or phenyl, cycloalkyl or phenyl, $A_3$ is

$R_4$ is hydrogen, alkyl, cycloalkyl, free, esterified or salified carboxy, cyano, phenyl or phenylalkyl, $A_4$ is

$R_4$ is —$R_5$—Y, $R_5$ is —O(CH$_2$)$_n$— in which n is 1, Y is —Y$_1$—B—Y$_2$ in which:

either $Y_1$ is phenylene optionally substituted by at least one member of the group consisting of alkyl, alkoxy, halogen, trifluoromethyl, cyano, or nitro, B is a single bond and $Y_2$ is phenyl carrying a substituent selected from the group consisting of tetrazolyl, CONH tetrazolyl, optionally esterified carboxy, alkyl, alkoxy, halogen, trifluoromethyl, cyano and nitro, or B is a single bond, $Y_2$ is hydrogen and $Y_1$ has the values of $Y_2$ $R_2$ and $R_3$ are selected from the group consisting of hydrogen; halogen; hydroxy; trifluoromethyl; cyano; nitro; alkyl of 1 to 4 carbon atoms optionally substituted by amino or dialkylamino containing 3 to 8 carbon atoms, hydroxyl, or alkoxy of 1 to 4 carbon atoms; alkoxy of 1 to 4 carbon atoms optionally substituted by fluorine; alkylthio of 1 to 6 carbon atoms; amino and carbamoyl optionally substituted by one or two alkyl to contain respectively at most 6 and 7 carbon atoms; carboxy; alkoxycarbonyl of 1 to 4 carbon atoms; acyl of 1 to 4 carbon atoms; acylamino of 1 to 4 carbon atoms and 3) 4-[[(2-butyl-4-quinolinyl)-oxy]-methyl]benzoic acid hydrochloride, Methyl 4'-[[(2-butyl-4-quinolinyl)-oxy](1,1'-biphenyl)-2-carboxylate, Methyl 4'-[[(3-butyl-5-methylthio-quinolinyl)-oxy]-methyl](1,1'-biphenyl)-2-carboxylate, Diethylamine salt of 4'-[[(3-butyl-1,4-dihydro-5-(methylthio)-4-quinolinyl)-oxy]-methyl](1,1'-biphenyl)-2-carboxylic acid and 4'-[[(3-butyl-4-quinolinyl)-oxy]-methyl](1,1'-biphenyl)-2-carboxylic acid.

It is understood that when $R_1$ is hydroxyl or mercapto,

can also be in the respective tautomeric forms of the oxo or thioxo radical.

In the products of formula I and in what follows: the term halogen is preferably chlorine, but can also be fluorine, bromine or iodine and the term acyl is preferably those of up to 7 carbon atoms such as acetyl, propionyl, butyryl or benzoyl, but can also be valeryl, hexanoyl, acryloyl, crotonoyl or carbamoyl or formyl.

The term esterified carboxy is preferably a lower alkoxy carbonyl such as methoxycarbonyl, ethoxycarbonyl, tert-butoxycarbonyl or benzyloxycarbonyl and the term cycloalkyl is preferably cyclopropyl, cyclopentyl or cyclohexyl but also cyclobutyl.

Alkyl is preferably methyl, ethyl, propyl, isopropyl, n-butyl, isobutyl, sec-butyl and tert-butyl but can also be pentyl or hexyl and particularly isopentyl and isohexyl and alkenyl is preferably vinyl, allyl, 1-propenyl, butenyl and particularly buten-1-yl, or pentenyl. Alkynyl is preferably ethynyl, propargyl, butynyl or pentynyl and alkoxy is preferably methoxy or ethoxy, but can also be propoxy, isopropoxy, linear, secondary or tertiary butoxy.

Acyloxy is an acyl as defined above and examples are acetoxy or propionyloxy. Alkylthio includes groups in which alkyl is for example, the values indicated above for alkyl and preferably is methylthio or ethylthio, but can also be propylthio, isopropylthio, n-butylthio, sec-butylthio, tert-butylthio, isopentylthio or isohexylthio.

Aryl is a carbocyclic or heterocyclic monocyclic or condensed rings, it being understood that the heterocyclic can contain one or more heteroatoms chosen from oxygen, nitrogen or sulfur and that when these heterocyclic contain more than one heteroatom, the heteroatoms of these heterocyclic can be identical or different. The monocyclic is preferably those which contain 5 or 6 ring members such as a carbocyclic monocyclic like phenyl and among the heterocyclic monocyclic are, for example, thienyl, furyl, pyrannyl, pyrrolyl, imidazolyl, pyrazolyl, pyridyl, pyrazinyl, pyrimidinyl, pyridazinyl, thiazolyl, oxazolyl, furazannyl, pyrrolinyl such as 2,3-dihydro pyrrolinyl, imidazolinyl such as 4,5-dihydro imidazolinyl, pyrazolinyl such as 2,3-dihydro pyrazolinyl as well as the position isomer of the heteroatom or heterotoms that these can contain such as, for example, isothiazolyl, or isoxazolyl.

The condensed rings are preferably those which contain 8 to 14 ring members such as carbocyclic condensed rings, there can be mentioned naphthyl and phenanthryl. Among the heterocyclic condensed rings, there can be mentioned benzothienyl, naphtho[2,3-b]thienyl, indanyl, indenyl, thianthrenyl, isobenzofurannyl, chromenyl, xanthenyl, phenoxathiinyl, indolizinyl, isoindolyl, 3H-indolyl, indolyl, indazolyl, purinyl, quinolizinyl, isoquinolyl, quinolyl, phthalazinyl, naphtyridinyl, quinoxalinyl, quinazolinyl cinnolinyl, pteridinyl, carbazolyl, etacarbolinyl, acridinyl, phenazinyl, phenothiazinyl, phenoxazinyl, indolinyl, isoindolinyl or also condensed polycyclic systems constituted by heterocyclic monocycles as defined, for example, above such as furo[2,3-b]pyrrole or thieno[2,3-b]furane.

Examples of such aryl are phenyl, naphthyl, thienyl such as thien-2-yl and thien-3-yl, furyl such as fur-2-yl, pyridyl such as pyrid-3-yl, pyrimidyl, pyrrolyl, thiazolyl, isothiazolyl, diazolyl, triazolyl, tetrazolyl, thiadiazolyl, thiatriazolyl, oxazolyl, oxadiazolyl, 3- or 4-isoxazolyl; condensed heterocyclic groups containing at least one heteroatom chosen from sulfur, nitrogen and oxygen, for example benzothienyl such as benzothien-3-yl, benzofuryl, benzopyrrolyl, benzimidazolyl, benzoxazolyl, thionaphthyl, indolyl or purinyl.

Such aryls can be optionally substituted such as N-substituted pyrrolyl, for example N-methylpyrrolyl, the substituted 3- or 4-isoxazolyl, for example, 3-aryl-5-methylisoxazol-4-yl, the aryl being, phenyl or halophenyl. The arylalkyl and arylalkenyl include those in which respectively the alkyl, alkenyl and aryl can have the values defined above. Examples of such arylalkyl are benzyl, diphenylmethyl, triphenylmethyl, naphthyl-methyl, indenylmethyl, thienylmethyl such as thien-2-yl-methyl, furylmethyl such as furfuryl, pyridylmethyl, pyrimidylmethyl or pyrrolylmethyl, it being understood that in the non-exhaustive list of examples of as mentioned above, the alkyl can also be ethyl, propyl or butyl such as in phenethyl.

Examples of arylalkenyl are the examples given above for arylalkyl in which the alkyl is replaced by an alkenyl such as in phenylvinyl or phenylallyl, it being understood that in these, the phenyl can also be replaced by naphthyl, pyridyl or also one of the aryls as defined above in the non-exhaustive list of arylalkyl.

The aryloxy and arylthio include those in which the aryl can take the values defined. In a non-exhaustive manner, there can be mentioned examples of such aryloxy and arylthio such as phenoxy, naphthyloxy, pyridyloxy, phenylthio and naphthylthio.

In the products of formula I and in what follows: the terms monocyclic and condensed rings are aryl being unsaturated carbocyclic or heterocyclic as defined above but also are saturated heterocyclic, it being understood that the heterocyclics as defined above can contain one or more heteroatoms chosen from oxygen, nitrogen or sulfur and that when these heterocyclics contain more than one hetroatom, the heteroatoms of these heterocyclics can be identical or different. Among the saturated heterocyclic monocyclics are pyrrolidinyl, imidazolidinyl, pyrazolidinyl, piperidyl, piperazinyl or morpholinyl. Among the saturated hetrocyclic condensed rings, there can be mentioned 1,10-diaza-4-anthryl.

The term alkylene is preferably methylene and ethylene but also n-propylene, isopropylene, n-butylene, isobutylene, secbutylene and tert-butylene. The alkylene can be optionally substituted, for example, by alkyl optionally substituted by an amino acid chosen from the natural amino acids such as, glycine, alanine, leucine, isoleucine, valine or phenylalanine.

The amino that can be one of the optional substituents of the substituents of the product of formula I and in what follows and that can be particularly

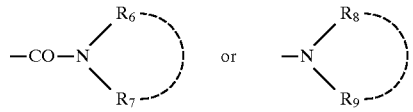

which two individual groups attached to the nitrogen are chosen from hydrogen; alkyl as defined above to give preferably monoalkyl- or dialkylamino in which the alkyl are 1 to 6 carbon atoms and particularly methyl, ethyl, isopropyl, trifluoromethyl, pentafluoroethyl, hydroxymethyl, hydroxyethyl, methoxymethyl, methoxyethyl, ethoxyethyl. The alkenyl as defined above and preferably vinyl and allyl or carbocyclic or heterocyclic aryl or arylalkyl defined above, and particularly phenyl, benzyl, phenethyl, naphthyl, indolyl, indolinyl, thienyl, furyl, pyrrolyl, pyridyl, pyrrolidinyl, piperidino, morpholino, piperazinyl, optionally substituted by one or more substituents as defined above such as methylpiperazinyl, fluoromethylpiperazinyl, ethylpiperazinyl, propylpiperazinyl, phenylpiperazinyl or benzylpiperazinyl.

When $R_6$ and $R_7$ on the one hand or $R_8$ and $R_9$ on the other hand form together with the nitrogen atom to which they are attached a heterocycle, examples include pyrrolyl, imidazolyl, pyridyl, pyrazinyl, pyrimidyl, indolyl, indolinyl, purinyl, quinolyl, pyrrolidinyl, piperidyl, piperidino, morpholino, piperazinyl which are optionally substituted by the substituents already previously mentioned and particularly by one or more chosen from chlorine and fluorine, methyl, ethyl, isopropyl, tert-butyl, methoxy, ethoxy, propoxy, benzoyl, methoxycarbonyl, ethoxycarbonyl, methylpiperazinyl, ethylpiperazinyl, propylpiperazinyl, phenylpiperazinyl or benzylpiperazinyl. In these last two, the phenyl and benzyl can be substituted as indicated previously for the aryl, arylalkyl and arylalkenyl.

The acyl of $R_8$ and $R_9$ are as defined previously and can be chosen for example from acetyl, propionyl, butyryl, valeryl or carbamoyl.

$Y_1$ and $Y_2$ can have the values defined above for the monocyclic aryl or condensed rings, it being understood that in the case where B is a single bond, $Y_2$ can also be non-cyclized such as hydrogen, cyano, or free, salified or esterified carboxy, the esterified carboxy preferably being a lower alkoxy carbonyl such as methoxycarbonyl, ethoxycarbonyl or benzyloxycarbonyl. $Y_1$ or $Y_2$ individually can be aryl optionally substituted by at least one member chosen, preferably, from halogen, hydroxyl, nitro, alkyl, alkenyl, alkoxy, acyl and free, salified or esterified carboxy of up to 6 carbon atoms and as defined above.

The addition salts with mineral or organic acids of the products of formula I can be salts formed with the following acids: hydrochloric acid, hydrobromic acid, hydroiodic acid, nitric acid, sulfuric acid, phosphoric acid, propionic acid, acetic acid, formic acid, benzoic acid, maleic acid, fumaric acid, succinic acid, tartaric acid, citric acid, oxalic acid, glyoxylic acid, aspartic acid, ascorbic acid, alkanemonosulfonic acids such as methanesulfonic acid, ethanesulfonic acid, propanesulfonic acid, alkanedisulfonic acids such as methanedisulfonic acid, alpha, betaethanedisulfonic acid, arylmonosulfonic acids such as benzenesulfonic acid and aryldisulfonic acids.

The carboxy(s) of the products of formula I can be salified by mineral bases such as an equivalent of sodium, potassium, lithium, calcium, magnesium or ammonium or by organic bases such as methylamine, propylamine, trimethylamine, diethylamine, triethylamine, N,N-dimethylethanolamine, tris(hydroxymethyl) amino methane, ethanolamine, pyridine, picoline, dicyclohexylamine, morpholine, benzylamine, procaine, lysine, arginine, histidine, N-methylglucamine.

The alkyl, alkenyl and alkynyl as defined above as well as the alkyl or alkenyl of the alkylthio, arylalkyl and arylalkenyl as defined above can be substituted by at least one substituent selected from the group consisting of halogen such as chloro or bromo, as in 2-bromoethyl; hydroxyl; aryl as defined above, that is a carbocyclic or heterocyclic monocyclic or condensed rings, it being understood that the heterocyclics as defined above can contain one or more heteroatoms chosen from oxygen, nitrogen or sulfur and that when these heterocyclics contain more than one heteroatom, the heteroatoms of these heterocyclics can be identical or different, the heterocyclic being able to be linked by a carbon atom or, if appropriate, by nitrogen; arylalkyl in which the aryl is as defined above; cycloalkyl such as cyclopropyl, cyclopentyl or cyclohexyl; cycloalkenyl such as cyclohexenyl can be optionally substituted such as 1,3-dimethyl-cyclohexenyl; alkoxy as defined above, such as methoxy, ethoxy, propoxy or isopropoxy as in, such as the methoxymethyl or 1-ethoxyethyl; substituted alkoxy such as trihaloalkoxy such as trifluoromethoxy; aryloxy, such as phenoxy; (arylalkyl)-oxy, such as benzyloxy; mercapto; alkylthio, such as methylthio or ethylthio; substituted alkylthio such as trihaloalkylthio such as trifluoromethylthio; arylthio; (arylalkyl)-thio; amino as in, 2-aminoethyl; amino substituted by one or two alkyl, alkenyl, aryl and arylalkyl as defined above such as monalkylamino in methylamino or ethylamino, such as dialkylamino in dimethylamino; nitro; cyano; azido; carboxy; esterified carboxy, such as methoxycarbonyl or ethoxycarbonyl; formyl; acyl, such as acetyl, propionyl or benzoyl; acyl substituted by an amino as defined above or by a cyclic linked to the acyl by nitrogen, this cyclic being able to optionally contain one or more heteroatoms chosen from nitrogen, oxygen or sulfur and as defined above; acyloxy, such as acetoxy or propionyloxy; carbamoyl; substituted carbamoyl, such as a lower N-monoalkyl carbamoyl such as N-methylcarbamoyl, N-ethylcarbamoyl, a lower N,N-dialkyl carbamoyl such as N,N-dimethylcarbamoyl, N,N-diethylcarbamoyl; N-(lower hydroxyalkyl) carbamoyl such as N-(hydroxymethyl) carbamoyl, N-(hydroxyethyl) carbamoyl, lower carbamoylalkyl such as carbamoylmethyl, carbamoylethyl; phth- limido; acylamido, such as acetamido or benzamido; alkoxycarbonylamino, such as methoxycarbonylamino or ethoxycarbonylamino; or (arylalkyl)-oxycarbonylamino, such as benzyloxycarbonylamino.

The aryl and alkoxy as defined above and the aryl of the arylalkyl and arylalkenyl as defined above, can be non-substituted or carry at least one member of the group consisting of for the optional substituents of the alkyl, alkenyl and alkynyl as defined above, such as o-chlorophenyl but can also be substituted by one or more chosen from the group formed by lower alkyl, such as methyl, ethyl, or also isopropyl or tert-butyl; alkenyl; substituted alkyl such as, trihaloalkyl as in trifluoromethyl; alkenyl such as vinyl or allyl; alkynyl such as propargyl.

The individual substituents that can be carried by a) the alkyl, alkenyl, alkynyl, alkoxy and alkylthyio of $R_{1B}$, $R_{2B}$, $R_{3B}$, $R_1$, $R_2$ and $R_3$, b) the aryl, arylalkyl, arylalkenyl, aryloxy and arylthio of $R_{1B}$, $R_{2B}$, $R_{3B}$, $R_1$, $R_2$ and $R_3$ and c) the alkyl, alkenyl and aryl of $R_{14}$ are chosen form the group consisting of halogen, hydroxyl, cyano, nitro, formyl, acyl or acyloxy of up to 6 carbon atoms, benzoyl, carboxy free, salified or esterified by alkyl of 1 to 6 carbon atoms, alkyl and alkenyl of up to 6 carbon atoms and optionally substituted by at least one member of the group consisting of halogen, hydroxyl and alkoxy of 1 to 6 carbon atoms, alkoxy and alkylthio of 1 to 6 carbon atoms, aryl and arylalkyl of 1 to 6 alkyl carbon atoms, the aryl being a monocyclic of 5 or 6 ring members or condensed rings of 8 to 10 ring members optionally contining one or more heteroatoms chosen from oxygen, nitrogen and sulfur and optionally substituted by one or more members chosen from halogen, hydroxyl, cyano, trifluoromethyl, nitro, alkyl, alkenyl, alkoxy and acyl of up to 6 carbon atoms, free, salified or esterified carboxyl,

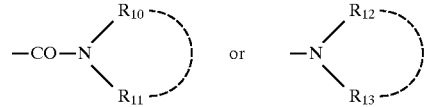

in which: either $R_{10}$ and $R_{11}$ or $R_{12}$ and $R_{13}$ individually are selected from the group consisting of hydrogen, alkyl or alkenyl of up to 6 carbon atoms and optionally substituted by at least one halogen or hydroxyl, alkyl or alkenyl of 2 to 6 carbon atoms substituted by alkoxy of 1 to 6 carbon atoms, aryl or arylalkyl of 1 to 6 alkyl carbon atoms, the aryl being a monocyclic of 5 or 6 ring members or condensed rings of 8 to 10 ring members optionally containing one or more heteroatoms chosen from oxygen, nitrogen and sulfur, and optionally substituted by at least one member of the group consisting of halogen, hydroxyl, cyano, trifluoromethyl, nitro, alkyl, alkenyl, alkoxy and acyl of up to 6 carbon atoms and free, salified or esterified carboxy, or $R_{10}$ and $R_{11}$ or $R_{12}$ and $R_{13}$ form respectively with the nitrogen atom to which they are attached a monocyclic of 5 or 6 ring members or condensed rings of 8 to 10 members optionally containing one or more heteroatoms chosen from oxygen, nitrogen and sulfur, and optionally substituted by one or more members chosen from halogen, hydroxyl, cyano, trifluoromethyl, nitro, alkyl, alkenyl, alkoxy and acyl of up to 6 carbon atoms, free, salified or esterified carboxy or $R_{12}$ and $R_{13}$ individually are acyl of a carboxylic acid of up to 6 carbon atoms, the said products of formula $I_B$ and I being in all possible racemic, enantiomeric and diastereoisomeric isomer forms, as well as their addition salts with mineral and organic acids or mineral and organic bases.

The

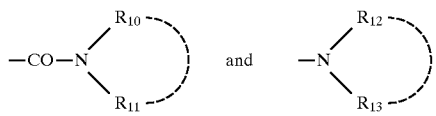

as defined above can have respectively the same values as those defined for

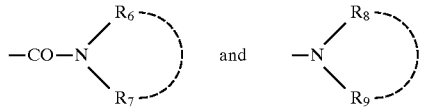

Among the subtituents which can be carried by alkyl, alkenyl, alkynyl, alkoxy, alkylthio, aryl, arylalkyl and arylalkenyl as defined above are more particularly halogen such as chloro and bromo; hydroxy; acyl such as acetyl, propionyl, butyryl, valeryl, hexanoyl, acryloyl, crotonoyl or carbamoyl; benzoyl; esterified carboxy of preferably lower alkoxy carbonyl such as methoxycarbonyl, ethoxycarbonyl or benzyloxycarbonyl; alkyl such as methyl or ethyl; amino; substituted amino such as substituted amino such as monoalkyl- and dialkylamino, such as methylamino, ethylamino or dimethylamino; alkyloxy, such as methoxy, ethoxy or isopropoxy; aryl such as phenyl, biphenyl, naphthyl, indenyl, indolyl or indolinyl; arylalkyl such as benzyl or phenethyl; alkyl, alkoxy and aryl as defined above being able to be substituted themselves by at least one member of the group consisting of hydroxyl, alkyl and alkoxy such as methyl, ethyl, tert-butyl, methoxy, ethoxy, isopropoxy; substituted amino such as monoalkyl, and dialkylamino, such as methylamino, ethylamino or carbocyclic or heterocyclic monocyclic of 6 ring members such as phenyl, pyrannyl, pyridyl, pyrimidinyl, pyridazinyl, pyrazinyl, piperidyl, piperazinyl, piperidino and morpholino; carbocyclic or heterocyclic monocyclic of 5 ring members such as furyl, pyrrolyl, pyrrolinyl, imidazolyl or pyrazolyl, isothiazolyl, isoxazolyl, pyrrolidinyl, imidazolidinyl, pyrazolidinyl; the carbocyclic or heterocyclic condensed rings among which are naphthyl, indolyl, quinolyl or purinyl as well as their position isomers of the heteroatom or heteroatoms, such as nitrogen such as indazolyl or isoquinolyl.

When such heterocyclics contain one or more nitrogen atoms. The nitrogen atoms can be non-substituted or one or more of the nitrogen atoms can be substituted, such as by alkyl or alkoxy of 1 to 5 carbon atoms as defined above, for example, methyl, ethyl, isopropyl, tert-butyl, methoxy or ethoxy, phenyl or benzyl optionally substituted by the substituents mentioned above for aryl and arylalkyl. There can be mentioned as examples methylpiperazinyl, ethylpiperazinyl, propylpiperazinyl, phenylpiperazinyl or benzylpiperazinyl.

Among the particularly preferred values for such groups are phenyl, naphthyl, pyridyl, piperazinyl, pyrimidinyl, pyridazinyl and pyrazinyl.

—$(CH_2)_{m1}$—$S(O)_{m2}$—X—$R_{14}$ in which $m_2$ is preferably 2, can represent alkylenes such as methylene, ethylene, n-propylene or n-butylene and $R_{14}$ is alkyl or alkenyl chosen from the values defined above or aryl also chosen from the values indicated above such as phenyl, biphenyl, naphthyl, tetrazolyl; the alkyl or alkenyl which can be $R_{14}$ can be optionally substituted by aryl chosen from the values defined above to form an aralkyl or aralkenyl.

The alkyl, alkenyl, aryl, aralkyl and arylalkenyl can be substituted themselves as is indicated above.

Examples are: —$CH_2SO_2$—$NH_2$ —$CH_2$—$SO_2$—NH—$C_6H_5$, —$SO_2$—NH—CO—NH—$CH_3$, —$SO_2$—NH—CO—NH—$C_6H_5$, —$SO_2$—NH—CO—NH—$CF_3$, —$SO_2NH$—CO—NH—$CH_2$—$C_6H_5$, —$SO_2$—NH—CO—NH—$C_6H_4Cl$, —$SO_2$—NH—CO—NH—$CH_2$, —$SO_2$—NH—CO—NH—CH=CH—$CH_3$,

—$SO_2NH$—CO—NH—$CH_2$—CH=CH
　　　　　　　　　　　　　　　　|　　|
　　　　　　　　　　　　　　　　A　 B in which A and B are individually chosen from hydrogen, phenyl, pyridyl and pyrimidyl;

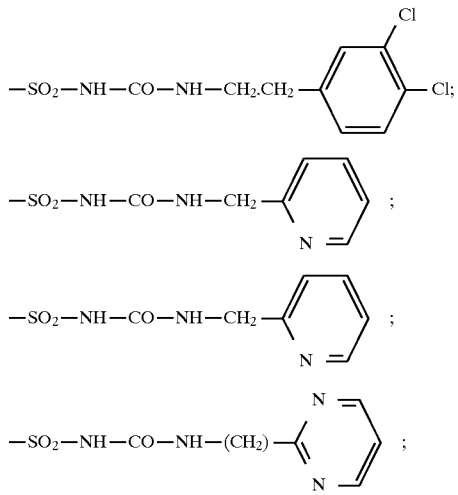

The aryl of $Y_{1B}$ can be substituted by one or more of the values of $R_{2B}$ and $R_{3B}$ and particularly by the following —$NH(CH_2)_{m1}$—$SO_2$—X—$R_{14}$ and CO—NH—$(CH_2)_{m1}$—$SO_2$—X—$R_{14}$ in which $(CH_2)_{m1}$—$SO_2$—X—$R_{14}$ can take the values indicated above.

There can be mentioned for example and in a non-exhaustive manner: —NH—$SO_2$—$CH_3$, —NH—$SO_2$—$C_6H_5$, —NH—$SO_2$—$CF_3$, —NH—$CH_2$—$SO_2$—NH—$C_6H_5$, —CO—NH—$SO_2$—$C_2H_5$, —CO—NH—$SO_2$—$CH_3$, —CO—NH—$SO_2$—$CH_2$—$C_6H_5$.

Therefore, the preferred compound of formula $I_B$ are those of quinoline in which one of $A_1$ and $A_4$ is nitrogen, of isoguinoline in which one of $A_2$ and $A_3$ is nitrogen and derivatives: of cinnoline in which $A_1$ and $A_2$ or $A_3$ and $A_4$ both are nitrogen, of quinoxaline in which $A_1$ and $A_4$ both are nitrogen, of quinazoline in which $A_1$ and $A_3$ or $A_2$ and $A_4$ both are nitrogen.

Particularly preferred are the products of the formula

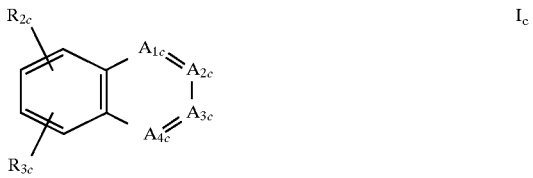

in which $R_{2c}$ and $R_{3c}$ are individually chosen from the group formed by hydrogen, halogen, hydroxyl, mercapto, cyano, nitro, formyl, benzoyl, acyl of up to 6 carbon atoms, carboxy free, salified or esterified by alkyl of 1 to 4 carbon atoms, alkyl, alkenyl, alkoxy and alkylthio of up to 6 carbon atoms, phenyl, naphthyl, benzyl and phenylthio optionally substituted by at least one member of the group consisting of halogen, hydroxyl, alkoxy of 1 to 4 carbon atoms, trifluoromethyl, cyano, acyl, free, salified or esterified carboxy, tetrazole, isoxazole, pyrrolidinyl, pyrrolidinylcarbonyl and phenyl optionally substituted by one or more members chosen from halogen, hydroxyl, alkyl and alkoxy of 1 to 4 carbon atoms, amino, mono- or dialkylamino, carbamoyl, pyrrolyl, morpholino, piperazinyl, pyrrolylmethyl, morpholinomethyl, piperazinylmethyl, pyrrolylcarbonyl, morpholinocarbonyl, pyrrolidinylcarbonyl, piperazinylcarbonyl, all the piperazinyl being optionally substituted on the second nitrogen atom by alkyl or phenyl optionally substituted by at least one member of the group consisting of halogen, hydroxyl, nitro, alkyl, alkoxy or acyl of up to 4 carbon atoms, trifluoromethyl, cyano, free, salified or esterified carboxy, tetrazole and isoxazole, $A_{1c}$, $A_{2c}$, $A_{3c}$ and $A_{4c}$ individually are nitrogen or

$R_{4c}$ is $R_{1a}$ such that $R_{1a}$ is selected from the group consisting of hydrogen, hydroxyl, cyano, carboxy free, salified or esterified by alkyl of 1 to 4 carbon atoms, alkyl, alkenyl, alkoxy, acyl or alkylthio of up to 7 carbon atoms, phenyl, benzyl, phenoxy, phenylthio, all the aliphatic or cyclic being optionally substituted by at least one member chosen from halogen, hydroxyl, nitro, alkyl, alkoxy or acyl of 1 to 4 carbon atoms, trifluoromethyl, cyano, carboxy free, salified or esterified by alkyl of 1 to 4 carbon atoms, tetrazole and isoxazole, or $R_{4c}$ is —C—$R_{5a}$—$Y_c$ in which: —$R_{5a}$ is —$CH_2$—, —NH—, —O—, —$OCH_2$— or —$SCH_2$— and $Y_c$ is phenylene optionally substituted by tetrazole or isoxazole or biphenyl optionally substituted by at least one member chosen from hydroxyl, halogen, alkyl and alkoxy of 1 to 4 carbon atoms, trifluoromethyl, cyano, nitro, free, salified or esterified carboxy, tetrazole, isoxazole and —$(CH_2)_p$—$SO_2$—$X_c$—$R_{14c}$, p is 0 or 1, $X_c$ is —NH—, —NH—CO—, —NH—CO—NH— or a single bond and $R_{14c}$ is selected from the group consisting of methyl, ethyl, propy, vinyl, allyl, pyridyl, phenyl, benzyl, pyridylmethyl or pyridylethyl, nitropyridyl, pyrimidyl, tetrazolyl, diazolyl, piperidinyl, alkylpiperidinyl, thiazolyl, alkylthiazolyl, tetrahydrofuranyl, methyltetrahydrofuranyl; amino or carbamoyl optionally substituted by one or two $(CH_2)_p$—$SO_2$—$X_c$—$R_{14c}$ as defined above or alkyl and alkenyl of up to 4 carbon atoms and optionally substituted; all optionally substituted by one or more substituents chosen from halogen, hydroxyl, alkyl, alkenyl and alkoxy of up to 4 carbon atoms, trifluoromethyl, cyano, free, salified or esterified carboxy and tetrazolyl; it being understood that:

1) the products of formula $I_c$ are such that at least one and at most two of $A_{1c}$, $A_{2c}$, $A_{3c}$ and $A_{4c}$ is nitrogen atom and at least one is methine substituted by —$R_{5a}$—$Y_c$, with the exception of the products in which:
   $A_{1c}$ is nitrogen,
   $A_{2c}$ is

$R_{4c}$ is selected from the group consisting of hydrogen, alkyl optionally substituted by one or more fluorine, hydroxyl or alkoxy of 1 to 4 carbon atoms or phenyl, $A_{3c}$ is

$R_{4c}$ is selected from the group consisting of hydrogen, alkyl, free, esterified or salified carboxy, cyano, nitro, phenyl or phenylalkyl,
$A_{4c}$ is

$R_{4c}$ is —$R_{5a}$—$Y_c$, $R_{5a}$ is —O—$CH_2$—, Y is phenyl optionally substituted by tetrazole or phenyl optionally substituted by a substituent chosen from the following tetrazolyl, optionally esterified carboxy, alkyl, alkoxy, halogen, trifluoromethyl, cyano and nitro,
$R_{2c}$ and $R_{3c}$ are chosen from hydrogen, halogen, hydroxyl, trifluoromethyl, cyano, nitro, alkyl of 1 to 4 carbon atoms optionally substituted by hydroxyl or alkoxy of 1 to 4 carbon atoms; alkoxy of 1 to 4 carbon atoms optionally substituted by fluorine; alkylthio of 1 to 6 carbon atoms; carbamoyl; amino optionally substituted by one or two alkyl of 1 to 6 carbon atoms; carboxy; alkoxycarbonyl of 1 to 4 carbon atoms; acyl of up to 4 carbon atoms.

3) The following 5 compounds:
4-[[(2-butyl-4-quinolinyl)-oxy]-methyl]benzoic acid hydrochloride.
Methyl 4'-[[2-butyl-4-quinolinyl)-oxy]-methyl](1,1'-biphenyl)-2-carboxylate.
Methyl 4'-[[(3-butyl-5-methylthio-4-quinolinyl)-oxy]-methyl](1,1'-biphenyl)-2-carboxylate.
Diethylamine salt of 4'-[[(3-butyl-1,4-dihydro-4-(methylthio)-4-quinolinyl)-oxy]-methyl](1,1'-biphenyl)-2-carboxylic acid.
4'-[[(3-butyl-4-quinolinyl)-oxy]-methyl](1,1'-biphenyl)-2-carboxylic acid.
Are part of the present invention, the said products of formula $I_c$ being in all possible racemic, enantiomeric and diastereoisomeric isomer forms, as well as their addition salts with mineral and organic acids or mineral and organic bases.

Another preferred group of compounds are those of the formula

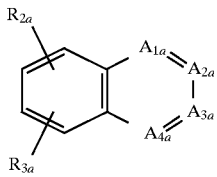

in which: $R_{2a}$ and $R_{3a}$ are individually chosen from the group consisting of: hydrogen, halogen, hydroxyl, mercapto, cyano, nitro, formyl, benzoyl, acyl of 1 to 6 carbon atoms, carboxy, free, salified or esterified by alkyl of 1 to 4 carbon atoms, alkyl, alkoxy and alkylthio of 1 to 6 carbon atoms, phenyl, naphthyl, benzyl and phenylthio, all optionally substituted by at least one member of the group consisting of halogen, hydroxy, alkoxy of 1 to 4 carbon atoms, trifluoromethyl, cyano, acyl, free, salified or esterified carboxy, tetrazole and isoxazole, amino, mono- or dialkylamino, carbamoyl, pyrrolyl, morpholino, piperazinyl, pyrrolylmethyl, morpholinomethyl, piperazinylmethyl, pyrrolylcarbonyl, morpholinocarbonyl, piperazinylcarbonyl, all the piperazinyl being optionally substituted on the second nitrogen atom by alkyl or phenyl optionally substituted by one or more chosen from halogen, hydroxyl, nitro, alkyl, alkoxy or acyl of 1 to 4 carbon atoms, trifluoromethyl, cyano, free, salified or esterified carboxy, tetrazole and isoxazole, $A_{1a}$, $A_{2a}$, $A_{3a}$ and $A_{4a}$ are individually nitrogen or —C—$R_{4a}$, $R_{4a}$ is $R_{1a}$ such that $R_{1a}$ is selected from the group consisting of hydrogen, hydroxyl, cyano, carboxy free, salified or esterified by alky of 1 to 4 carbon atoms, alkyl, alkenyl, alkoxy, acyl or alkylthio of up to 7 carbon atoms, phenyl, benzyl, phenoxy, phenylthio all these optionally substituted by at least one member of the group consisting of halogen, hydroxyl, nitro, alkyl, alkoxy or acyl of 1 to 4 carbon atoms, trifluoromethyl, cyano, carboxy free, salified or esterified by alkyl of 1 to 4 carbon atoms, tetrazole and isoxazole or $R_{4a}$ is —C—$R_{5a}$—$Y_a$, —$R_{5a}$ is —$CH_2$—, —NH—, —O—, —$OCH_2$— or —$SCH_2$— and $Y_a$ is phenyl substituted by tetrazole or isoxazole or biphenyl optionally substituted by one member chosen from the group consisting of hydroxyl, halogen, alkyl and alkoxy of 1 to 4 carbon atoms, trifluoromethyl, cyano, nitro, free, salified or esterified carboxy, tetrazole or isoxazole, it being understood that:

1) the products of formula $I_a$ are such that of $A_{1a}$, $A_{2a}$, $A_{3a}$ and $A_{4a}$ at least one and at most two is nitrogen and at least one is methine substituted by —$R_{5a}$—$Y_a$, with the exception of the products in which:

$A_{1a}$ is nitrogen, $A_{2a}$ is

$R_{4a}$ is hydrogen, alkyl optionally substituted by one or more fluorine, hydroxyl or alkoxy of 1 to 4 carbon atoms or phenyl, $A_{3a}$ is

$R_{4a}$ is hydrogen, alkyl, free, esterified or salified carboxy, cyano, nitro, phenyl or phenylalkyl, $A_{4a}$ is

$R_{4a}$ is —$R_{5a}$—$Ya_c$, $R_{5a}$ is —O—$CH_2$—, $Y_a$ is phenyl optionally substituted by tetrazole or phenyl optionally substituted by a substituent chosen from the tetrazolyl, optionally esterified carboxy, alkyl, alkoxy, halogen, trifluoromethyl, cyano and nitro, $R_{2a}$ and $R_{3a}$ are chosen from the group consisting of hydrogen; halogen; hydroxyl; trifluoromethyl; cyano; nitro; alkyl of 1 to 4 carbon atoms optionally substituted by hydroxyl or alkoxy of 1 to 4 carbon atoms; alkoxy of 1 to 4 carbon atoms optionally substituted by fluorine; alkylthio of 1 to 6 carbon atoms; carbamoyl; amino optionally substituted by one or two alkyl of up to 6 carbon atoms; carboxy; alkoxycarbonyl of up to 4 carbon atoms; acyl of up to 4 carbon atoms.

3) The following 5 compounds:

4-[[(2-butyl-4-quinolinyl)-oxy]-methyl]benzoic acid hydrochloride.

Methyl 4'-[[2-butyl-4-quinolinyl)-oxy]-methyl](1,1'-biphenyl)-2-carboxylate.

Methyl 4'-[[(3-butyl-5-methylthio-4-quinolinyl)-oxy]-methyl](1,1'-biphenyl)-2-carboxylate.

Diethylamine salt of 4'-[[(3-butyl-1,4-dihydro-4-(methylthio)-4-quinolinyl)-oxy]-methyl](1,1'-biphenyl)-2-carboxylic acid and 4'-[[(3-butyl-4-quinolinyl)-oxy]-methyl](1,1'-biphenyl)-2-carboxylic acid, are part of the present invention, the said products of formula $I_a$ being in all possible racemic, enantiomeric and diastereoisomeric isomer forms, as well as their addition salts with mineral and organic acids or mineral and organic bases.

Most preferred compounds of formula I are those wherein:

$R_2$ and $R_3$ are hydrogen or alkylthio of 1 to 4 carbon atoms, $A_1$, $A_2$ and $A_3$ are such that one or two are nitrogen, and the others individually are

$R_4$ is chosen from hydrogen, n-butyl and alkylthio of 1 to 4 carbon atoms, and $A_4$ is —C—$R_5$—Y, $R_5$ is —$CH_2$—, —NH—, —O— or —$OCH_2$— and Y is phenyl substituted by tetrazole or biphenyl optionally substituted by at least one of cyano, free, salified and esterified carboxy and tetrazolyl with the exception of products in which:

$A_1$ is nitrogen, $A_2$ is

$R_4$ is hydrogen or n-butyl, $A_3$ is =C—$R_4$, $R_4$ is hydrogen or n-butyl, $A_4$ is

$R_4$ is —$R_5$—Y, $R_5$ is —O—$CH_2$—,

Y is phenyl optionally substituted by tetrazole or phenyl optionally substituted by a substituent chosen from tetrazolyl, optionally esterified carboxyl and cyano, $R_2$ and $R_3$ are chosen from hydrogen or alkylthio of 1 to 4 carbon atoms, it being understood that the following 5 compounds:

4-[[(2-butyl-4-quinolinyl)-oxy]-methyl]benzoic acid hydrochloride,

Methyl 4'-[[2-butyl-4-quinolinyl)-oxy]-methyl](1,1'-biphenyl)-2-carboxylate,

Methyl 4'-[[(3-butyl-5-methylthio-4-quinolinyl)-oxy]-methyl](1,1'-biphenyl)-2-carboxylate, Diethylamine salt of 4'-[[(3-butyl-1,4-dihydro-4-(methylthio)-4-quinolinyl)-oxy]-methyl](1,1'-biphenyl)-2-carboxylic acid, 4'-[[(3-butyl-4-quinolinyl)-oxy]-methyl](1,1-'biphenyl)-2-carboxylic acid, are part of the present invention, the said products of formula I being in all possible racemic, enantiomeric and diastereoisomeric isomer forms, as well as their addition salts with mineral and organic acids or mineral and organic bases.

A specific preferred compound of the invention is:
4'-[(2-butyl-4-quinolinyl)-methyl](1,1'-biphenyl)-2-carboxylic acid.

The process of the invention for the preparation of a compound of formula $I_B$ comprises reacting
a) either a compound of the formula

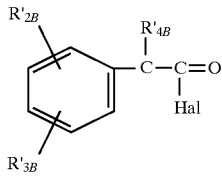

III in which $R_{2B'}$, $R_{3B'}$ and $R_{4B'}$ have the above meanings respectively for $R_{2B}$, $R_{3B}$ and $R_{4B}$ in which the optional reactive functions are optionally protected by protective groups and Hal is halogen to a substitution reaction to obtain a product of the formula

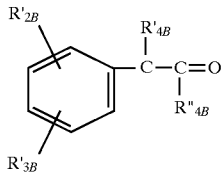

IV in which $R_{2B'}$, $R_{3B'}$ and $R_{4B'}$ have the above meanings and $R_{4B''}$ is $R_{4B'}$, has the meaning for $R_{4B}$ in which the optional reactive functions are optionally protected by protective groups, reacting the latter: with a compound of the formula

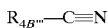

$R_{4B'''}$—C≡N    V in which $R_{4B'''}$, identical or different to $R_{4B'}$ or $R_{4B''}$, has the meaning of $R_{4B}$ in which the optional reactive functions are optionally protected by protective groups to obtain, after cyclization, a product of the formula

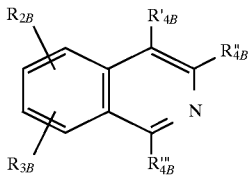

Ii in which $R_{2B'}$, $R_{3B'}$, $R_{4B'}$, $R_{4B''}$ and $R_{4B'''}$ have the above meanings
b) or a product of the formula

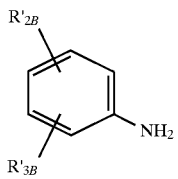

VI in which $R_{2B'}$ and $R_{3B'}$ have the above meanings with a product of the formula

$R_{4B'}$—CH(CO$_2$alk)—CO—$R_{4B''}$    VII in which $R_{4B'}$ and $R_{4B''}$ individually have the above meanings and alk is alkyl of 1 to 6 carbon atoms to obtain a product of the formula

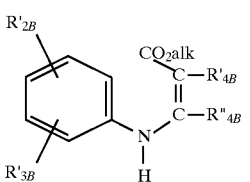

VIII in which $R_{2B'}$, $R_{3B'}$, $R_{4B'}$, $R_{4B''}$ and alk have the above meanings which is cyclized to obtain a product of the formula

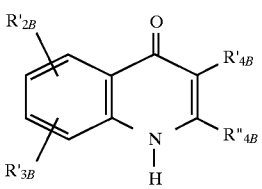

IIb in which $R_{2B'}$, $R_{3B'}$, $R_{4B'}$ and $R_{4B''}$ have the above meanings
c) or a product of the formula

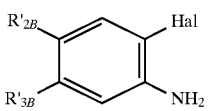

IX in which $R_{2B'}$ and $R_{3B'}$ have the above meanings with a product of the formula

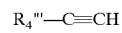

$R_{4}'''$—C≡CH    X in which $R_{4'''}$ has the above meaning to obtain a product of the formula

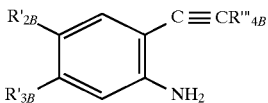

XI in which $R_{2B'}$, $R_{3B'}$ and $R_{4B'''}$ have the above meanings which is subjected to a cyclization reaction in the presence of a nitrogen donor such as sodium nitrite to obtain a product of the formula

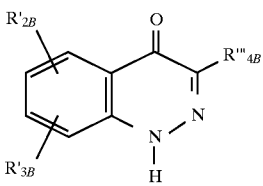

IIc in which $R_{2B'}$, $R_{3B'}$ and $R_{4B'''}$ have the above meanings
d) or a product of the formula

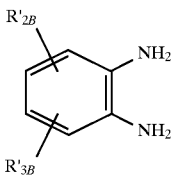

XII in which $R_{2B'}$ and $R_{3B'}$ have the above meanings with a product of the formula

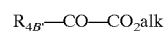

$R_{4B'}$—CO—CO$_2$alk    XIII in which $R_{4B'}$ and alk have the above meanings to obtain, after cyclization, a product of the formula

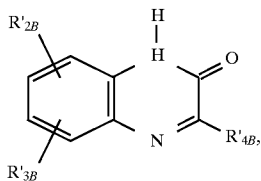

in which $R_{2B'}$, $R_{3B'}$ and $R_{4B'}$ have the above meanings e) or a product of the formula

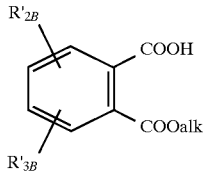

in which $R_{2B'}$ and $R_{3B'}$ and alk have the above meanings is subjected, after, optionally a halogenation reaction of the free carboxy function, to an addition reaction on this carboxy function of a compound of formula $R_{4B'}$, $R_{4B'}$ having the above meaning to obtain, after cyclization in the presence of hydrazine or a derivative of the products of formula

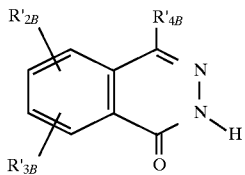

in which $R_{2B'}$, $R_{3B'}$ and $R_{4B'}$ have the above meanings f) or a product of the formula

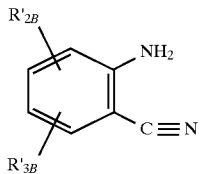

in which $R_{2B'}$ and $R_{3B'}$ have the above meanings with a product of the formula

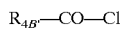

in which $R_{4B'}$ has the above meaning to obtain a product of the formula

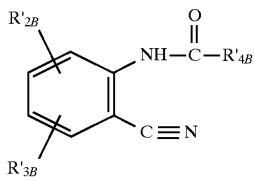

in which $R_{2B'}$, $R_{3B'}$ and $R_{4B'}$ have the above meanings to obtain, after cyclization, a product of the formula

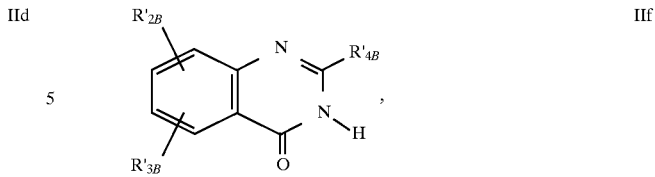

in which $R_{2B'}$, $R_{3B'}$ and $R_{4B'}$ have the above meanings which products of formula $I_i$ can be products of formula $I_B$ and products of formulae $II_b$, $II_c$, $II_d$, $II_e$ and $II_f$ as defined above which can be products of formula $I_B$ in which at least one of $A_{1B}$, $A_{2B}$, $A_{3B}$ and $A_{4B}$ is methine substituted with hydroxyl, which are subjected, if desired and if necessary, to one or more of the following reactions in any order:

a complete reduction reaction of the hydroxyl or oxo into methine followed by aromatization, on the products of formula $I_i$ in which one of $R_{4B'}$, $R_{4B''}$ or $R_{4B'''}$ is hydroxyl or on the products of formulae $II_b$, $II_c$, $II_d$, $II_e$ and $II_f$ which are subjected either first to a substitution reaction of the hydroxyl by halogen followed by the action of a product of the formula $R_{p4}$-M-Hal in which $R_{p4}$ has the above meaning for $R_{4B}$ in which the optional reactive functions are optionally protected by protective groups, M is a metal chosen from magnesium, copper and zinc and Hal is halogen, or to the action of a product of formula $R_{p4}$-Hal in which Hal is halogen in order to obtain the corresponding products of formula I, a conversion reaction of a (=O) oxo function into a (=S) thioxo function, an elimination reaction of the protective groups that can be carried by the protected reactive functions, a salification reaction by a mineral or organic acid or by a mineral or orgnaic base to obtain the corresponding salt, an esterification reaction of an acid function, a saponification reaction of an ester function into an acid function, a conversion reaction of an alkoxy function into a hydroxyl function, a conversion reaction of the cyano into an acid, a reduction reaction of the carboxy into an alcohol, a resolution reaction of the racemic forms, the said products of formula $I_B$ thus obtained being in all possible racemic, enantiomer and diastereoisomeric isomer forms.

In the preferred conditions for the invention, the process is carried out in the following manner: the substitution reaction on the halogen derivative of formula III to obtain the product of formula IV can be carried out according to the usual known methods such as by the reaction of an organometallic compound such as an organozinc of the formula Zn—Br—$R_{4B''}$ on the acid chloride of formula III or also particularly when $R_{4B''}$ is butyl, by the reaction of a tin derivative such as the compound of formula $Sn(R_{4B''})_4$ preferably in the presence of palladium in a solvent such as ether or tetrahydrofuran, the addition reaction of the compound of formula V on the compound of formula IV can be carried out by the usual known methods such as in phosphoryl trichloride in the presence of a Lewis acid and the cyclization reaction giving the product of formula $I_i$ takes place in situ, The addition reaction of the compound of formula VII on the compound of formula VI can be carried out according to the usual known methods such as in the presence of a drying agent such as a molecular sieve or also an acid such as p-toluene sulfonic acid, and the cyclization reaction of the compound of formula VIII into a compound of formula IIb can be carried out for example in a solvent such as diphenylether DOWTHERM or also in absence of a solvent by taking the compound to its melting point.

The addition reaction of the compound of formula X to the compound of formula IX to obtain the compound of formula XI can be carried out in the presence of a copper salt preferably in the presence of a catalyst such as a palladium catalyst in a basic solvent such as triethylamine or diethylisopropylamine and the cyclization reaction of the compound of formula XI into a compound of formula IIc can be carried out in the presence of a nitrogen donor such as sodium nitrite in an acid medium such as in hydrochloric acid.

The addition reaction of the compound of formula XIII to the compound of formula XII can be carried out in a solvent such as toluene or tetrahydrofuran preferably in the presence of a drying agent such as a molecular sieve, the cyclization reaction which gives the compound of formula IId taking place in situ, and the halogenation reaction of the compound of formula XIV can be carried out by the usual known methods such as in the presence of oxalyl chloride or also thionyl chloride and the cyclization of the compound obtained to give the compound of formula IIe takes place in the presence of hydrazine or a derivative of hydrazine while hot in an alcohol such as methanol or ethanol. The addition reaction of the acid chloride of formula XVI on the amine derivative of formula XV to obtain the compound of formula XVII can be carried out at reflux of a solvent such as pyridine, and the cyclization reaction of the product of formula XVII to obtain the product of formula IIf takes place in hydrogen peroxide in the presence of aqueous sodium hydroxide at reflux in a solvent such as dioxane.

The products of formula Ii are products of formula $I_B$ in which $A_{1B'}$, $A_{2B'}$, $A_{3B'}$ and $A_{4B'}$ can be —C—$R_{4B'}$, —C—$R_{4B''}$ or —C—$R_{4B'''}$ as defined above or the meanings indicated respectively for $A_{1B}$, $A_{2B}$, $A_{3B}$ and $A_{4B}$ in which the optional reactive functions are optionally protected by the protective groups and in which at least one of $A_{1B}$, $A_{2B}$, $A_{3B}$ and $A_{4B}$ is methine carrying hydroxyl.

The products of formula Ii and the products of formulae IIb, IIc, IId, IIe and IIf particularly to give the products of formula $I_B$ can be subjected, if desired and if necessary, to one or more of the reactions indicated above which can be in the preferred conditions carried out in the manner indicated hereafter.

The existing hydroxyls or those resulting from the oxo tautomer form of the compounds of formuale IIb, IIc, IId, IIe and IIf or optionally from the products of formula Ii obtained as indicated above can be, if necessary and if desired, subjected to a complete reduction reaction into methine. This complete reduction reaction into methine as defined above can be carried out after conversion of the hydroxyl function into halogen or mesylate using a reducing agent such as lithium aluminium hydride or also by catalytic reduction on palladium in the presence of hydrogen.

The substitution reaction of the products of formulae Ii, IIb, IIc, IId, IIe,and IIf by $R_{4p}$ is subjected beforehand to a substitution reaction of the hydroxyl carried out by preparing the halogen derivative such as the chlorinated derivative prepared by treatment with a chlorinating agent such as phosphorous pentachloride or phosphorous oxychloride optionally in a solvent such as dioxane or tetrahydrofuran or also carried out by the addition of the hydroxyl by the preparation of trifluoroacetate sulfonate.

The substitution reaction by $R_{4p}$ as defined above can be carried out by reaction with an organometallic compound such as an organozinc of the formula $R_{4p}$—Zn—Br if desired in the presence of catalytic quantity of a transition metal complex such as palladium or nickel at reflux of a solvent such as tetrahydrofuran.

The conversion reaction of the oxo function into a thioxo function can be carried out by the usual known methods such as using Lawesson's reagent or also phosphorous pentasulfide at reflux in a solvent such as toluene or an alcohol such as ethanol.

The various reactive functions that can be carried by certain compounds of the reactions defined above can, if necessary, be protected. It may be hydroxyl, acyl, free carboxy or also amino and monoalkylamino which can be protected by suitable protective groups. The following non-exhaustive list of examples of protection of the reactive functions can be mentioned: hydroxyls can be protected by alkyl, trialkylsilyl, dihydropyran, methoxymethyl or tetrahydropyrannyl, the amino groups can be protected by acetyl, trityl, benzyl, tert-butoxycarbonyl, phthalimido or other groups known in the chemistry of the peptides. The acyl groups such as formyl can be protected in the form of cyclic or non-cyclic ketals such as dimethyl- or diethylketal or ethylene dioxyketal and the acid functions of the products can be, if desired, amidified by a primary or secondary amine for example in methylene chloride in the presence of 1-ethyl-3-(dimethylaminopropyl) carbodiimide hydrochloride at ambient temperature. The acid functions can be protected in the form of esters formed with easily cleavable esters such as benzyl or tert-butyl esters or esters known in the chemistry of the peptides.

The elimination of these protective groups is carried out in the usual known conditions, notably acid hydrolysis with an acid such as hydrochloric acid, benzenesulfonic acid or p-toluenesulfonic acid, formic acid or trifluoroacetic acid.

The phthalimido group is eliminated by hydrazine and a list of various usable protective groups will be found for example in the Patent No. BF 2,499,995.

The products described above can optionally be subjected to salification reaction with a mineral or organic acid or by a mineral or organic base, particularly on the optional carboxy functions, these reactions being able to be carried out by the usual known methods.

The products can, if desired, be subjected, on the optional carboxy functions, to esterification reactions which can be carried out by the usual known methods. The optional ester functions of the products can be, if desired, saponified into an acid function, these saponification reactions being able to be carried out in the usual known conditions notably by alkaline or acid hydrolysis for example by sodium hydroxide or potassium hydroxide in an alcoholic medium such as in methanol or also by hydrochloric acid or sulfuric acid.

The optional alkoxy such as methoxy of the products can be, if desired, converted into hydroxyl or alcohol function by known conditions by boron tribromide in a solvent such as methylene chloride, by pyridine hydrobromide or hydrochloride or also by hydrobromic acid or hydrochloric acid in water or acetic acid at reflux.

The optional cyano of the products can be, if desired, converted into an acid function by the usual known conditions by hydrolysis carried out in an acid medium such as in a mixture of sulfuric acid, glacial acetic acid and water, these three compounds being preferably in equal proportions, or also in a mixture of sodium hydroxide, ethanol and water at reflux.

The optional esterified carboxy of the products can, if desired, be reduced into an alcohol by known methods and notably by lithium aluminium hydride in a solvent such as tetrahyrofuran or also dioxane or ethyl ether.

The optional carboxy functions of the products can, if desired, be reduced into an alcohol by known methods and thus can be first esterified, then converted into an alcohol as indicated above.

The optional optically active forms of the products of formula $I_B$ can be prepared by resolution of the racemics by the usual methods.

The novel compositions of the invention for antagonizing the effects of angiotensin II receptors are comprised of an amount of at least one compound of formula $I_B$ and its non-toxic, pharmaceutically acceptable salts sufficient to antagonize the effects of angiotensin II receptors and an inert pharmaceutical carrier. The compositions may be in the form of tablets, dragees, capsules, granules, suppositories, injectable solutions, ointments, creams, gels and aerosol properties.

Examples of suitable excipients are talc, arabic gum, lactose, starch, magnesium stearate, cocoa butter, aqueous or non-aqueous vehicles, fatty substances of animal or vegetable origin, paraffin derivatives, glycols, various wetting agents, dispersants or emulsifiers and preservatives.

The compositions are inhibitors of the effects of angiotensin II, particularly the vasoconstrictive effect and also the trophic effect at the level of the myocytes. Certain products of the invention also possess antagonistic properties for the endotheline receptor and are notably antagonistic of the vasoconstrictive effect of endotheline. The compounds of formulae $I_B$ and I also possess the property of improving the cognitive functions.

The compositions are useful in the treatment of cardiovascular illnesses presenting an alteration of vasomotricity: myocardium infarct, cardiac insufficiency, renal insufficiency, angina pectoris, cerebral vascular spasm, Raynaud's disease, arterial hypertension and all illnesses following an ischemia. They are also useful in the treatment of glaucoma, atherosclerosis, asthma and various types of visceral spasms, as well as neuromal protective substances or also in the prevention of post-angioplastic restenoses and can be used in the treatment of certain gastrointestinal and gynaecological disorders and particularly for a relaxing effect at the level of the uterus as well as in the treatment of memory disorders, senile dementia and Alzheimer's disease.

The novel method of the invention for inhibiting the effect of angiotensin II in warm-blooded animals, including humans, comprises administering to warm-blooded animals an amount of at least one compound of formula $I_B$ and its non-toxic, pharmaceutically acceptable salts sufficient to inhibit the effects of angiotensin II. The products may be administered orally, rectally, parenterally or topically to the skin and mucous membranes. The usual daily dose is 0.013 to 1.33 mg/kg depending on the condition treated, the method of administration and the specific compound used.

The starting compounds of formulae III, V, VI, VII, IX, X, XII, XIII, XIV, XV and XVI are commercially available or can be prepared by known methods. The compounds of formula III can be derivatives of phenylacetyl chloride and such compounds of formula III are described in the literature such as Org. Synth. 1972, p. 36 and Can. J. Chem. 1957, Vol. 35, p. 651.

The compounds of formula V can be nitrile-type derivatives which can be prepared as described in Synthesis 1987, p. 514. The compounds of formula VI can be aniline derivatives which can be found commercially. For example, certain compounds of formula VI such as when one of $R_2$ or $R_3$ is carbomethoxy, such as methyl anthranilate or methyl 3-aminobenzoate are marketed for example by Aldrich.

The compounds of formula VII can be esters derived from formylacetic acid which can be prepared as in J. Het. Chem. 1983, Vol. 20, p. 623 or Liebigs Ann. Chem. 1966, Vol. 697, p. 62.

The compounds of formula IX can be ortho halo aniline derivatives which can be prepared as in Ann. Chim. 1962, Vol. 52, p. 727. The compounds of formula X can be acetylene derivatives prepared as described in J. Am. Chem. Soc., 1937, Vol. 59, p. 1490.

Among the compounds of formula XII which can be found commercially are methyl 3,4-diaminobenzoate which is marketed by LANCASTER. The said compounds may be prepared as described in Org. Synth 1943, p. 501.

The compounds of formula XIII can be glyoxylic acid derivatives prepared as described in J. Org. Chem. 1979, Vol. 44, p. 1613. The compounds of formula XIV can be phthalic acid derivatives and may be prepared as described in J. Org. Chem. 1963, Vol. 28, p. 582 or J. Chem. Soc., 1952, p. 553.

The compounds of formula XV can be cyanoaniline derivatives which can be found commercially such as 2-aminobenzonitrile sold by Aldrich, or 5-chloro-2-cyanoaniline sold by Bayer. The compounds of formula XVI can be acyl chloride derivatives and can be prepared as described in Org. Synth. Coll. Vol. III, p 190.

On the other hand, certain intermediate products can be found commercially such as chlorinated derivatives like 4-chloro-2-phenylquinazoline sold by ALDRICH and may be prepared as described in J. Org. Chem., Vol. 37, p. 1681 (1972).

4-chloro-2-phenylquinazoline enables the products of formula I derived from 2-phenylquinazoline to be prepared into which, by the intermediary for example of an organometallic compound such as $R_4$—Zn—Br, $R_4$ being as defined above can be introduced by substitution on the chlorine atom or of a trifluoromethane sulfonate under the usual known conditions.

The products of formula $I_B$ are such that $A_{1B}$, $A_{2B}$, $A_{3B}$ and $A_{4B}$ are nitrogen or methine substituted by $R_{4B}$. When $R_{4B}$ is —$R_5$—$Y_B$ and particularly is biphenylmethyl, a preparation process of such a radical can consist of subjecting methyl iodobenzoate to the action of iodotoluene, the reaction being carried out in the presence of powdered copper at a temperature of about 100° C. to 300° C. to obtain a product of formula

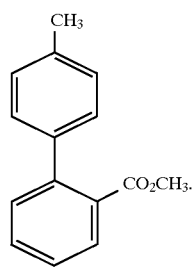

c the esterified carboxy of which can, if desired, be freed from the alkyl by standard known methods or as indicated above by acid or alkaline hydrolysis which can be subjected to a bromination reaction on the methyl by standard known methods by the action of n-bromosuccinimide in carbon tetrachloride. Preparation examples of such compounds of formula —$R_5$—Y as defined above are described in the literature and examples are given in particular in U.S. Pat. No. 4,880,804.

The novel intermediates of the invention are the compounds of formulae VIII, IIb, IIc, IId, IIe and IIf.

A preferred method of the invention for inhibiting the effects of angiotensin II in warm-blooded animals comprising administering to the animals an effective amount of a compound of the formula

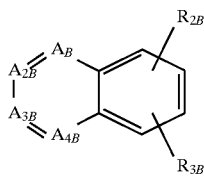   F$_B$ in which:

R$_{2B}$ and R$_{3B}$ are individually selected from the group consisting of
a) hydrogen, halogen, hydroxyl, mercapto, cyano, nitro, sulfo, formyl, benzoyl, acyl of up to 12 carbon atoms, free, salified or esterified carboxy, cycloalkyl of 3 to 7 carbon atoms, acyloxy of up to 12 carbon atoms,
b) alkyl, alkenyl, alkynyl, alkoxy or alkylthio of up to 6 carbon atoms and optionally substituted,
c) aryl, arylalkyl, arylalkenyl, aryloxy or arylthio of 1 to 6 alkyl and alkenyl carbon atoms, the aryl being a monocyclic of 5 or 6 ring member or condensed rings of 8 to 10 ring members optionally containing one or more heteroatoms chosen from oxygen, nitrogen and sulfur, and optionally substituted,

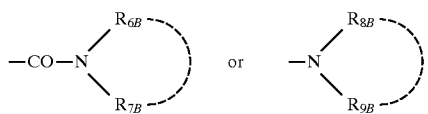   d)

in which:

either R$_{6B}$, and R$_{7B}$ or R$_{8B}$ and R$_{9B}$ are individually selected from the group consisting of hydrogen, alkyl or alkenyl of up to 6 carbon atoms and optionally substituted by at least one halogen or hydroxyl, alkyl or alkenyl of 2 to 6 carbon atoms substituted by alkoxy of 1 to 6 carbon atoms, aryl or arylalkyl with 1 to 6 alkyl carbon atoms, aryl being a monocyclic of 5 or 6 ring members or condensed rings of 8 to 10 ring members optionally containing one or more heteroatoms chosen from oxygen, nitrogen and sulfur, and optionally substituted by at least one member of the group consisting of halogen, hydroxyl, cyano, trifluoromethyl, nitro, alkyl, alkenyl, alkoxy, alkylthio and acyl of up to 6 carbon atoms, free, salified or esterified carboxy, —(CH$_2$)$_{m1}$—S(O)$_{m2}$—X—R$_{14}$, $_{m1}$ is an integer from 0 to 4, and $_{m2}$ is an integer from 0 to 2, and either —X—R$_{14}$ is —NH$_2$, or X is —NH—, —NH—CO, —NH—CO—NH— or a single bond and R$_{14}$ is alkyl, alkenyl or aryl optionally substituted, or R$_{6B}$ and R$_{7B}$ or R$_{8B}$ and R$_{9B}$ form respectively with the nitrogen atom to which they are linked a monocyclic of 5 or 6 ring members or condensed rings of 8 to 10 ring members optionally containing one or more heteroatoms chosen from oxygen, nitrogen and sulfur, and optionally substituted by at least one member of the group consisting of halogen, hydroxyl, cyano, trifluoromethyl, alkyl, alkenyl, alkoxy, alkylthio and acyl of up to 6 carbon atoms, free, salified or esterified carboxy, e) —(CH$_2$)$_{m1}$—S(O)$_{m2}$—X—R$_{14}$, or R$_{8B}$ and R$_{9B}$ are individually an acyl of a carboxylic acid of up to 6 carbon atoms, A$_{1B}$, A$_{2B}$, A$_{3B}$ and A$_{4B}$ are individually nitrogen or

=C—R$_{4B}$, either R$_{4B}$ is R$_1$ such that R$_1$ is selected from the group consisting of
a) hydrogen, hydroxyl, cyano, benzoyl, acyl of up to 12 carbon atoms, free, salified or esterified carboxy, cycloalkyl of 3 to 7 carbon atoms,
b) alkyl, alkenyl, alkynyl, alkoxy or alkylthio of up to 6 carbon atoms and optionally substituted,
c) aryl, arylalkyl, arylalkenyl, aryloxy or arylthio of up to 6 alkyl and alkenyl carbon atoms, the aryl being a monocyclic of 5 or 6 ring members or condensed rings of 8 to 10 ring members optionally containing one or more heteroatoms chosen from oxygen, nitrogen and sulfur and optionally substituted, or R$_{4B}$ is —R$_5$—Y$_B$ such that:
—R$_5$ is selected from the group consisting of
a) alkylene of up to 4 carbon atoms and optionally substituted by at least one halogen, oxo and —OZ in which Z is hydrogen or alkyl of 1 to 4 carbon atoms optionally substituted by an amino acid,
b) —NH—, —O(CH$_2$)$_n$—, or —S(CH$_2$)$_n$—, n is an integer from 0 to 4, Y$_B$ is —Y$_{1B}$—B—Y$_{2B}$ in which: Y$_1$ is a monocyclic aryl of 5 or 6 ring members or condensed rings of 8 to 10 ring members optionally containing one or more heteroatoms chosen from oxygen, nitrogen and sulfur, and optionally substituted by at least one of R$_{2B}$ or R$_{3B}$, B is either a single bond between Y$_1$ and Y$_2$, or —CO—, —CO—NH—, —NH—CO—, —NH(CH$_2$)$_n$—, —O—(CH$_2$)$_n$— or —S—(CH$_2$)$_n$—, n is 0 to 4, Y$_{2B}$ is either, if B is a single bond, hydrogen or halogen, hydroxyl, cyano, nitro, trifluoromethyl, free, salified or esterified carboxy, tetrazole or isoxazole, or, whatever the value of B and Y$_{2B}$ being identical to or different from Y$_{1B}$, the values defined for Y$_{1B}$, the said products of formula F$_B$ being in all possible racemic, enantiomeric and diastereoisomeric isomer forms, as well as their addition salts with mineral and organic acids or with mineral and organic bases, for medicaments intended, either for the treatment of arterial hypertension, cardiac insufficiencies, renal insufficiencies and in prevention of post-angioplastic restenoses, or for the treatment of certain gastrointestinal or gynaecological disorders.

A more particular preferred method of the invention is the use of the products of the formula

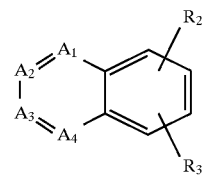   F in which:

R$_2$ and R$_3$ are individually selected from the group consisting of
a) hydrogen, halogen, hydroxyl, mercapto, cyano, nitro, sulfo, formyl, benzoyl, acyl of up to 12 carbon atoms, free, salified or esterified carboxy, cycloalkyl of 3 to 7 carbon atoms,
b) alkyl, alkenyl, alkynyl, alkoxy or alkylthio of up to 6 carbon atoms and optionally substituted,
c) aryl, arylalkyl, arylalkenyl, aryloxy or arylthio with 1 to 6 alkyl and alkenyl carbon atoms, the aryl being a monocyclic of 5 or 6 ring members or condensed rings of 8 to 10 ring members optionally containing one or more heteroatoms chosen from oxygen, nitrogen and sulfur, and optionally substituted,

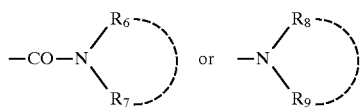 d)

in which:
either $R_6$ and $R_7$ or $R_8$ and $R_9$ are individually selected from the group consisting of hydrogen, alkyl or alkenyl of up to 6 carbon atoms and optionally substituted by at least one halogen or hydroxyl, alkyl or alkenyl of 2 to 6 carbon atoms substituted by alkoxy of 1 to 6 carbon atoms, aryl or arylalkyl with 1 to 6 alkyl carbon atoms, the aryl being a monocyclic of 5 or 6 ring members or condensed rings containing 8 to 10 ring members optionally containing one or more heteroatoms chosen from oxygen, nitrogen and sulfur, and optionally substituted by at least one member of the group consisting of halogen, hydroxyl, cyano, trifluoromethyl, nitro, alkyl, alkenyl, alkoxy, alkylthio and acyl of up to 6 carbon atoms, free, salified or esterified carboxy, or $R_6$ and $R_7$ or $R_8$ and $R_9$ form respectively with the nitrogen atom to which they are attached a monocyclic of 5 or 6 ring members or condensed rings of 8 to 10 ring members optionally containing one or more heteroatoms chosen from oxygen, nitrogen and sulfur, and optionally substituted by at least one member of the group consisting of halogen, hydroxyl, cyano, trifluoromethyl, nitro, alkyl, alkenyl, alkoxy, alkylthio and acyl of up to 6 carbon atoms, free, salified or esterified carboxy,
or $R_8$ and $R_9$ are individually acyl of a carboxylic acid of up to 6 carbon atoms, $A_1$, $A_2$, $A_3$ and $A_4$ are individually nitrogen or

either $R_4$ is $R_1$ such that $R_1$ is selected from the group consisting of
a) hydrogen, hydroxyl, cyano, benzoyl, acyl of up to 12 carbon atoms, free, salified or esterified carboxy, cycloalkyl of 3 to 7 carbon atoms,
b) alkyl, alkenyl, alkynyl, alkoxy or alkylthio of up to 6 carbon atoms and optionally substituted,
c) aryl, arylalkyl, arylalkenyl, aryloxy or arylthio of up to 6 alkyl and alkenyl carbon atoms, the aryl being a monocyclic of 5 or 6 ring members or condensed rings of 8 to 10 ring members optionally containing one or more heteroatoms chosen from oxygen, nitrogen and sulfur, and optionally substituted or $R_4$ is —$R_5$—Y, —$R_5$ is selected from the group consisting of
a) divalent alkylene of up to 4 carbon atoms and optionally substituted by at least one halogen or oxo or —OZ, Z is hydrogen or alkyl of 1 to 4 carbon atoms optionally substituted by an amino acid,
b) —NH—, —O($CH_2$)$_n$— or —S($CH_2$)$_n$—, n is an integer from 0 to 4, Y is —$Y_1$—B —$Y_2$,
$Y_1$ is a monocyclic aryl of 5 or 6 ring members or condensed rings of 8 to 10 ring members optionally containing one or more heteroatoms chosen from oxygen, nitrogen and sulfur, and optionally substituted by at least one of $R_2$ or $R_3$,
B is either a single bond between $Y_1$ and $Y_2$, or —CO—, —CO—NH—, —NH—CO—, —NH—($CH_2$)$_n$—, or —O—($CH_2$)$_n$ or —S($CH_2$)$_n$, n is an integer from 0 to 4, $Y_2$ is either, if B is a single bond, hydrogen or halogen, hydroxyl, cyano, nitro, trifluoromethyl, free, salified or esterified carboxy, tetrazole or isoxazole, or whatever the value of B and $Y_2$ being identical to or different from $Y_1$, the values defined for $Y_1$, the said products of formula F being in all possible racemic, enantiomeric and diastereoisomeric isomer forms, as well as their addition salts with mineral and organic acids or mineral and organic bases useful either for the treatment of arterial hypertension, cardiac insufficiencies, renal insufficiencies and in the prevention of post-angioplastic restenoses, or for the treatment of certain gastrointestinal or gynaecological disorders as well as for the treatment of arterial hypertension, cardiac insufficiencies, renal insufficiencies and the prevention of post-angioplastic restenoses.

A more preferred method of the invention is the use of a compound of the formula

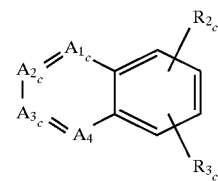 Fc in which:
$R_{2c}$ and $R_{3c}$ are individually chosen from the group consisting of hydrogen, halogen, hydroxyl, mercapto, cyano, nitro, formyl, benzoyl, acyl of up to 6 carbon atoms, carboxy free, salified or esterified by alkyl of 1 to 4 carbon atoms, alkyl, alkenyl, alkoxy and alkylthio of up to 6 carbon atoms, phenyl, naphthyl, benzyl, phenylthio, all optionally substituted by at least one member of the group consisting of halogen, hydroxyl, alkoxy of 1 to 4 carbon atoms, trifluoromethyl, cyano, acyl, free, salified or esterified carboxy, tetrazole, isoxazole, pyrrolidinyl, pyrrolidinylcarbonyl and phenyl optionally substituted by one or more of halogen, hydroxyl and alkyl and alkoxy of 1 to 4 carbon atoms, amino, mono- or dialkylamino, carbamoyl, pyrrolyl, morpholino, piperazinyl, pyrrolymethyl, morpholinomethyl, piperazinylmethyl, pyrrolylcarbonyl, morpholinocarbonyl, pyrrolidinylcarbonyl, piperazinylcarbonyl, all the piperazinyl being optionally substituted on the second nitrogen atom by an alkyl or phenyl optionally substituted by at least one member of the group consisting of halogen, hydroxyl, nitro, alkyl, alkoxy or acyl of up to 4 carbon atoms, trifluoromethyl, cyano, free, salified or esterified carboxy, tetrazole and isoxazole, $A_{1c}$, $A_{2c}$, $A_{3c}$ and $A_{4c}$ are individually nitrogen or

either $R_{4c}$ is $R_{1a}$ such that $R_{1a}$ is selected from the group consisting of hydrogen, hydroxyl, cyano, carboxy free, salified or esterified by alkyl of 1 to 4 carbon atoms, alkyl, alkenyl, alkoxy, acyl or alkylthio of up to 7 carbon atoms, phenyl, benzyl, phenoxy, phenylthio, all optionally substituted by at least one member of the group consisting of halogen, hydroxyl, nitro, alkyl, alkoxy or acyl of 1 to 4 carbon atoms, trifluoromethyl, cyano, carboxy free, salified or esterified by alkyl of 1 to 4 carbon atoms, tetrazole and isoxazole,
or $R_{4c}$ is —C—$R_{5a}$—$Y_c$, —$R_{5a}$ is —$CH_2$—, —NH—, —O—, —$OCH_2$— or $SCH_2$— and —$Y_c$ is phenyl or biphenyl optionally substituted by at least one member of the group consisting of hydroxyl, halogen, alkyl and alkoxy of 1 to 4 carbon atoms, trifluoromethyl, cyano, nitro, free, salified or esterified carboxy, tetrazole, isoxazole, and —(CH$_2$)$_p$—SO$_2$—X$_c$—R$_{14c}$, p is 0 or 1, X$_c$ is —NH—, —NH—CO or —NH—CO—NH— or a single bond and R$_{14c}$ is selected from the group consisting of methyl, ethyl, vinyl, allyl, pyridyl, phenyl, benzyl, pyridylmethyl or pyridylethyl, all optionally substituted by at least one halogen or hydroxyl or alkyl and alkoxy of 1 to 4 carbon atom or trifluoromethyl, the said products of formula (Fc) being in all possible racemic, enantiomeric and diastereoisomeric isomer forms, as well as their addition salts with mineral and organic acids or mineral and organic bases.

Another more particular group of compounds of the invention are compounds of the formula

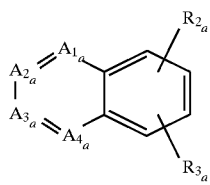

in which:

R$_{2a}$ and R$_{3a}$ are individually chosen from the group formed by hydrogen, halogen, hydroxy, mercapto, cyano, nitro, formyl, benzoyl, acyl of up to 6 carbon atoms carboxy, free, salified or esterified by alkyl of 1 to 4 carbon atoms, alkyl, alkoxy and alkylthio of up to 6 carbon atoms, phenyl, naphthyl, benzyl and phenylthio, all optionally substituted by at least one member of the group consisting of halogen, hydroxyl, alkoxy of 1 to 4 carbon atoms, trifluoromethyl, cyano, acyl, free, salified or esterified carboxy, tetrazole and isoxazole, amino, mono- or dialkylamino, carbamoyl, pyrrolyl, morpholino, piperazinyl, pyrrolylmethyl, morpholinomethyl, piperazinylmethyl, pyrrolylcarbonyl, morpholinocarbonyl, piperazinylcarbonyl, all the piperazinyl being optionally substituted on the second nitrogen atom by alkyl or phenyl optionally substituted by at least one member of the group consisting of halogen, hydroxyl, nitro, alkyl, alkoxy or acyl of up to 4 carbon atoms, trifluoromethyhl, cyano, free, salified or esterified carboxy, tetrazole and isoxazole, A$_{1a}$, A$_{2a}$, A$_{3a}$ and A$_{4a}$ are individually nitrogen or

either R$_{4a}$ is R$_{1a}$ such that R$_{1a}$ is selected from the group consisting of hydrogen, hydroxyl, cyano, carboxy free, salified or esterified by alkyl of 1 to 4 carbon atoms, alkyl, alkenyl, alkoxy, acyl or alkylthio of up to 7 carbon atoms, phenyl, benzyl phenoxy, phenylthio, all optionally substituted by at least one member of the group consisting of halogen, hydroxyl, nitro, alkyl, alkoxy or acyl of up to 4 carbon atoms, trifluoromethyl, cyano carboxy free, salified or esterified by alkyl of 1 to 4 carbon atoms, tetrazole and isoxazole, R$_{4a}$ is

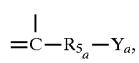

—R$_{5a}$ is —CH$_2$—, —NH—, —O—, —OCH$_2$— or —SCH$_2$— and Y$_a$ is phenyl or biphenyl optionally substituted by at least one member of the group consisting of hydroxyl, halogen, alkyl and alkoxy of 1 to 4 carbon atoms, trifluoromethyl, cyano, nitro, free, salified or esterified carboxy, tetrazole and isoxazole, the said products of formula Fa being in all possible racemic, enantiomeric and diastereoisomeric isomer forms, as well as their addition salts with mineral and organic acids or mineral and organic bases.

Among the products of formula I$_B$ which are particularly preferred are the products corresponding to the formulae indicated below in which R$_{2B}$, R$_{3B}$ and —R$_5$—Y$_B$ have the above meanings and n-bu is n-butyl:

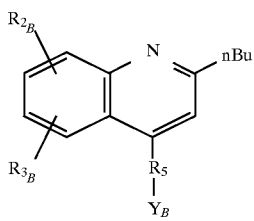

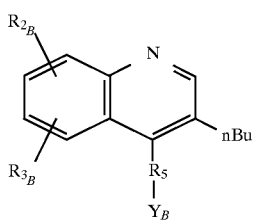

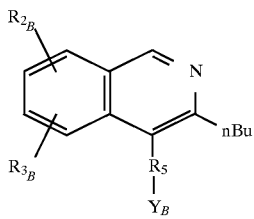

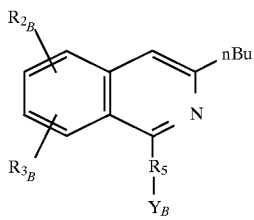

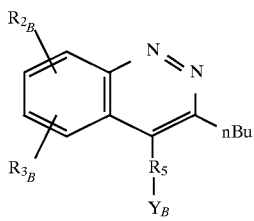

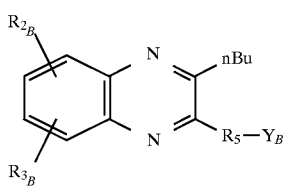

-continued

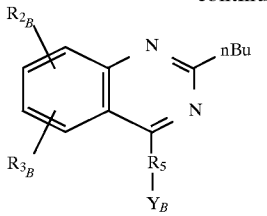

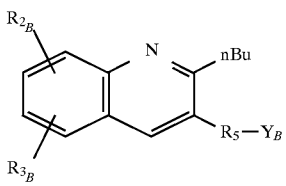

Among the products whose formulae are indicated above, $Y_B$ is particularly biphenyl substituted by free, salified or esterified carboxy, cyano, optionally salified tetrazolyl or $-(CH_2)_{m1}-SO_2-X-R_{14}$ as defined above.

In the following examples, there are described several preferred embodiments to illustrate the invention. However, it should be understood that the invention is not intended to be limited to the specific embodiments.

EXAMPLE 1

Methyl 4'-[(3-butyl-4-quinolinyl)-methyl]-1,1'-biphenyl-2-carboxylate

STEP A: Diethyl 2-butyl-3-oxo-butanedioate 100 ml of ether, then 13.55 ml of diethyl oxalate were added to a solution of sodium ethylate prepared by stirring 2.3 g of sodium and 150 ml of ethanol at 40° C. for one hour. The mixture was refluxed for 15 minutes, cooled down slightly and 50 ml of ethyl caproate were added. The mixture was stirred at reflux for 3 hours and at 30° C. to 35° C. for 16 hours. 50 ml of water were added and the aqueous phase was separated by decanting, washed twice with ether and acidified with 2N hydrochloric acid. Extraction was carried out 3 times with ether and the combined organic phases were washed with water, then with a saturated solution of sodium chloride, dried and evaporated to dryness to obtain 9.5 g of the desired product which was used as is for the following step.

STEP B: Diethyl 2-butyl-3-(phenylamino)-2-butanedioate

A mixture of 1 g of aniline was stirred for 3 days at 75° C. with 2.65 g of the product of Step A and 150 mg of siliporite® NK 10. Then, the reaction mixture was cooled and chromatographed on silica (eluant:hexane-ethyl acetate 9-1) to obtain 1.55 g of the expected product.

IR Spectrum (CHCl₃):

| =C—NH | 3260 cm⁻¹ |
| C=O | 1733, 1656 cm⁻¹ |
| C=C + aromatic | 1610, 1596, 1584, 1500 cm⁻¹ |

STEP C: Ethyl 3-butyl-1,4-dihydro-4-oxo-2-quinoline carboxylate and ethyl 3-butyl-4-hydroxy-2-quinoline carboxylate A mixture of 2.5 g of the product of Step B and 30 ml of diphenylether was heated for 30 minutes using a metallic bath at 250° C. The mixture was allowed to return to ambient temperature, was separated and washed with pentane to obtain 1.82 g of the desired product.

IR Spectrum (CHCl₃):

| =C—NH | 3425, 3383 cm⁻¹ |
| C=O | 1746, 1706 cm⁻¹ |
| other C=O, | 1624, 1605, 1585, 1572, 1532 cm⁻¹ |
| C=C, aromatic | |

STEP D: 3-butyl-1,4-dihydro-4-oxo-2-quinolinecarboxylic acid 1.8 g of the ester of Step C were heated for one hour at 60° C. with 25 ml of N sodium hydroxide solution and the mixture was cooled and acidified with N hydrochloric acid, filtered, washed with water and dried at 60° C. under reduced pressure to obtain 1.58 g of the desired product.

NMR Spectrum (60 mHz, DMSO, ppm):

| 0.89 (t) | CH₃—CH₂—CH₂—CH₂ |
| 1.39 (m) | C—C—C—C |
| 2.78 | C—C—C—C— |
| 7.30 (t)–7.63 (t) | H₆ and H₇ |
| 7.80 (d)–8.08 (d) | H₅ and H₈ |
| 11.64 | mobile proton |

STEP E: 3-butyl-4(1H)-quinolone

A mixture of 1.55 g of the product of Step D and 10 ml of diphenylether was heated for 30 minutes at 250° C. and the mixture was cooled, filtered, washed with pentane and dried under reduced pressure to obtain 1.17 g of product which was dissolved in 80 ml of ethanol. The solution was heated for 15 minutes at reflux in the presence of activated charcoal, followed by filtering on hyflosupercel. The ethanol was evaporated to dryness and the residue was taken up in pentane, filtered, washed with pentane and dried at 50° C. under reduced pressure to obtain 0.971 g of the desired product.

IR Spectrum (CHCl₃):

| =C—NH | 3440 cm⁻¹ |
| other C=O, | 1632, 1590, 1570, 1558, 1524, 1506 cm⁻¹ |
| C=C, aromatic | |

STEP F: 3-butyl-4-chloro quinoline

A mixture of 515 mg of the product of Step E with 0.6 ml of phosphorous oxychloride was heated for 2 hours at 120° C. and the mixture was cooled. 10 ml of water were added and alkalization was carried out to pH 9 with concentrated ammonium hydroxide. Extraction was carried out twice with methylene chloride and the extracts were washed with a saturated solution of sodium chloride, dried and evaporated to dryness. The residue was dissolved in 30 ml of ethanol and treated for 15 minutes at reflux in the presence of activated charcoal, followed by filtration on hyflosupercel to obtain 511 mg of the desired product.

NMR CDCl₃ (250 MHz)

| CH₃—CH₂—CH₂—CH₂—C— | 0.98 (t) |
| CH₃—CH₂—CH₂—CH₂—C— | 1.45 (m) |
| CH₃—CH₂—CH₂—CH₂—C— | 1.68 (m) |
| CH₃—CH₂—CH₂—CH₂—C— | 2.96 (m) |
| aromatic H's | 7.63 (dt) |
| | 7.72 (dt) |
| | 8.10 (dd) |
| | 8.25 (dd) |
| pyridine nucleus H | 8.74 (s) |

STEP G: Methyl 4'-[[3-butyl-4-quinolinyl]-methyl](1,1'-biphenyl)-2-carboxylate 475 mg of electrolytic zinc, 275 mg of tetrakis (triphenylphosphine) palladium, 2.08 g of methyl 4-(bromomethyl)-1,1-biphenyl-2-carboxylate (prepared in EP 0,025,331)) were introduced into 13 ml of tetrahydrofuran. 503 mg of 3-butyl-4-chloro quinoline of Step F were introduced and the mixture was stirred for 15 hours in an ultrasonic bath, allowing the temperature to rise to 65° C. 50 ml of 0.1N hydrochloric acid were added and extraction was carried out with ethyl acetate. The extracts were washed with a saturated solution of sodium chloride, dried and evaporated to dryness. After chromatography on silica (eluant: choloroform-hexane-ethyl acetate 100-100-10), 624 mg of the expected product were obtained.

IR Spectrum (CHCl$_3$):

| COOMe | 1720 to 1436 cm$^{-1}$ |
| aromatic and heterocycle | 1615, 1600, 1574, 1508 cm$^{-1}$ |

EXAMPLE 2

4'-[(3-butyl-4-quinolinyl)-methyl](1,1'-biphenyl)-2-carboxylic acid 550 mg of the product of Example 1 were introduced into 16 ml of sodium hydroxide and 3 ml of methanol and the mixture was stirred for 3 hours and 30 minutes at a temperature of 80° C. 1 ml of sodium hydroxide and 1 ml of methanol were added and the mixture was heated again for 7 hours. The methanol was evaporated off and the mixture was taken up in water and acidified with concentrated hydrochloric acid and filtered. The precipitate was taken up in water and washed with water and dried under reduced pressure at 60° C. for 24 hours. The precipitate was dissolved by heating in 50 ml of methylene chloride. Filtration was carried out, followed by evaporation and chromatography on silica (eluant:methylene chloride on its own, then methylene chloride-methanol 9-1). The eluate was filtered, evaporated and the residue was taken up in ether. The crystallized product was dried under reduced pressure at 60° C. in the presence of phosphorous pentoxide to obtain 422 mg of the expected product.

IR Spectrum (Nujol):

| C=O | 1695 cm$^{-1}$ |
| aromatics + heterocyclic | 1610, 1595, 1575, 1510 cm$^{-1}$ |

Analysis: C$_{27}$H$_{25}$NO$_2$; molecular weight=395.51

| Calculated | % C | 81.09 | % H | 6.37 | % N | 3.54 |
| Found: | | 82.00 | | 6.30 | | 3.40 |

EXAMPLE 3

Methyl 4'-[(2-butyl-4-quinolinyl)-methyl]-1,1'-biphenyl-2-carboxylate

STEP A 70.8 g of ethyl carbonate dissolved in 50 ml of ether were added to a suspension of 27.3 g of 50% sodium hydride in oil previously washed with heptane and 250 ml of ether and the mixture was stirred for 10 minutes. 30 g of hexanone were added over 30 minutes and the mixture was refluxed for 2 hours. 35 ml of ether containing 12 ml of ethanol were added and the mixture was stirred for 16 hours at ambient temperature. After cooling to 0° C., a solution of 36 ml of acetic acid in 300 ml of water was added and then 12 ml of a saturated solution of sodium bicarbonate were added. The pH was then 7 and extraction was carried out with ether. The extracts were washed with water, dried and evaporated to dryness and after distillation at 70° C. under a reduced pressure of 3 mbar, 32.5 g of the desired product were obtained.

NMR Spectrum:

| CH$_3$—CH$_2$ | 0.91 ppm |
| central CH$_2$'s | 1.34–1.59 ppm |
| CH$_2$—C<br>‖<br>O | 2.55 ppm (t) |
| CO$_2$Et | 1.28 ppm (t)<br>4.20 ppm (q) |
| C—CH$_2$—C<br>‖    ‖<br>O    O | 3.44 ppm (s) |

STEP B: Ethyl 3-(phenylamino)-2-heptanoate

Using the procedure of Step B of Example 1, 45 g of the product of Step A were reacted to obtain after chromatographing on silica (eluant:hexane-ethyl acetate (95-5)), 28.7 g of the expected product.

IR Spectrum (CHCl$_3$):

| NH | 3260 cm$^{-1}$ |
| C=O | 1648 cm$^{-1}$ |
| C=C + aromatic | 1612, 1594, 1588 cm$^{-1}$ |

STEP C: 2-butyl-4(1H)-quinolone

Using the procedure of Step C of Example 1, 28.7 g of the compound of Step B were reacted to obtain 16.95 g of the desired product melting at 140° C.

IR Spectrum (CHCl$_3$):

| =C—NH | 3428 cm$^{-1}$ + strong general absorption |
| C=O + C=C + C=N + aromatics | 1636, 1596, 1547, 1502 cm$^{-1}$ |

STEP D: 4-chloro-2-butyl quinoline

Using the procedure of Step F of Example 1, 4 g of the compound of Step C were reacted to obtain 3.89 g of the desired product.

NMR (CDCl$_3$):

| CH$_3$—CH$_2$—CH$_2$—CH$_2$ | 0.97 (t) |
| CH$_3$—CH$_2$—CH$_2$—CH$_2$ | 1.45 (m) |
| CH$_3$—CH$_2$—CH$_2$—CH$_2$ | 1.72 (m) |
| CH$_3$—CH$_2$—CH$_2$—CH$_2$ | 2.95 (m) |
| aromatic H's | 7.41 (dt) |
| | 7.74 (dt) |
| | 8.06 (dd) |
| | 8.19 (dd) |
| pyridine H | 7.41 (s) |

STEP E: Methyl 4'-[[2-butyl-4-quinolinyl]-methyl]1,1'-biphenyl-2-carboxylate

Using the procedure of Step G of Example 1, 500 mg of 2-butyl-4-chloro quinoline of Step D were introduced into a previously prepared solution of 475 mg of electrolytic zinc, 275 mg of tetrakistriphenyl-phosphine palladium and 2.075 g of [[2'-(methoxycarbonyl)(1,1'-biphenyl)-4-yl]-methyl zinc bromide prepared as in Example 1 in 13 ml of tetrahydrofuran. After chromatographing on silica (eluant:choloroform-hexane-ethyl acetate 100-100-10), 621 mg of the expected product were obtained.

IR Spectrum (CHCl$_3$):

| —COOMe | 1720, 1435 cm$^{-1}$ |
|---|---|
| aromatics + heteroccyclic | 1602, 1560, 1508, 1480 cm$^{-1}$ |

EXAMPLE 4

4'-[(2-butyl-4-quinolinyl)-methyl](1,1'-biphenyl)-2-carboxylic acid 614 mg of the product of Example 3 were introduced into 10 ml of 1N sodium hydroxide and 10 ml of ethanol and the mixture was heated at 70° C. for 2 hours. The ethanol was evaporated off and the residue was taken up in water and acidified with 1N hydrochloric acid. The precipitate was filtered off, washed with water and dried under reduced pressure at 60° C. The precipitate was taken up in ethanol at reflux and treated with activated charcoal. After filtration, it was evaporated and chromatographed on silica (eluant:methylene chloride-ethanol 9-1) to obtain after crystallization from ether, 363 mg of the expected product.

Preparation of the hydrochloride

The product was taken up in 20 ml of 0.1N sodium hydroxide and 10 ml of N sodium hydroxide and the clear solution was acidified to pH=1 with concentrated hydrochloric acid. The white precipitate was filtered off, washed in water and dried under reduced pressure at 60° C. Crystallization from ether was carried out and filtration was carried out again to obtain 180 mg of the expected hydrochloride melting at 227° C.

Analysis: C$_{27}$H$_{25}$NO$_2$; molecular weight=395.51

| Calculated | % C | 81.99 | % H | 6.37 | % N | 3.54 |
|---|---|---|---|---|---|---|
| Found: | | 81.8 | | 6.50 | | 3.40 |

Analysis: C$_{27}$H$_{26}$NClO$_2$; molecular weight=431.97

| Calculated | % C | 75.07 | % H | 6.06 | % N | 3.24 | % Cl | 8.21 |
|---|---|---|---|---|---|---|---|---|
| Found: | | 75.4 | | 6.1 | | 3.1 | | 8.1 |

IR Spectrum (Nujol):

| Absorption OH/NH region | approx. 2640 cm$^{-1}$ |
|---|---|
| C=O complex | 1725 cm$^{-1}$ (sh), 1720 cm$^{-1}$ (max) |
| | 1708 cm$^{-1}$ (max) |
| aromatics + heteroccyclic | 1640, 1600, 1518, 1495 cm$^{-1}$ |

EXAMPLE 5

4-[(3-butyl-4-quinolinyl)-amino]-benzoic acid 0.520 g of the product of Step F of Example 1 and 0.390 g of 4-amino benzoic acid were introduced into 6 ml of 2N hydrochloric acid and the solution was refluxed for 63 hours. The precipitate was filtered off, washed with water and taken up in 10 ml of 2N sodium hydroxide in 40 ml of water, then washed with ethyl acetate. The aqueous phase was taken up in acetic acid and the precipitate was filtered, washed with water, separated out and taken up in ether. After drying, 220 mg of the expected product melting at 276° C. were obtained.

Preparation of the hydrochloride 156 mg of the product in 10 ml of a 50-50 mixture of methylene chloride-ethanol was stirred and then taken to reflux and filtered. After evaporation, the dry extract was taken up in 96% ethanol and concentrated hydrochloric acid was added until a pH of about 1 was reached. Evaporation was carried out again and crystallization from ether took place. After filtration, then drying under reduced pressure at 65° C., 162 mg of the expected hydrochloride were obtained.

Analysis: C$_{20}$H$_{20}$N$_2$O$_2$; molecular weight=356.85

| Calculated | % C | 67.32 | % H | 5.93 | % N | 7.85 | % Cl | 9.93 |
|---|---|---|---|---|---|---|---|---|
| Found: | | 67.0 | | 6.0 | | 7.6 | | 10.0 |

IR Spectrum (Nujol):

| OH/NH | 3260 cm$^{-1}$ |
|---|---|
| —C=O | 1736, 1668 cm$^{-1}$ |
| aromatics, heterocyclic and NH$_2$ | 1605, 1570, 1518, 1500 cm$^{-1}$ |

EXAMPLE 6

4-[[(2-butyl-4-quinolinyl)-oxy]-methyl]-benzonitrile 0.6 g of the product of Step C of Example 3 were introduced into 30 ml of anhydrous acetone and 0.828 g of potassium carbonate were added. The mixture was stirred for 10 minutes and 1.16 g of 4-(bromomethyl) benzonitrile were added. The reaction medium was refluxed for 3 hours and the acetone was evaporated off. The residue was taken up in 100 ml of water and the aqueous phase was extracted 3 times with 50 ml of ethyl acetate. The organic phase was washed with 100 ml of a saturated solution of ammonium chloride, dried and evaporated. After chromatography on silica (eluant:methylene chloride-methanol 98-2), 0.78 g of the expected product melting at 74° C. were obtained.

IR Spectrum (CHCl$_3$):

| C≡N | 2236 cm$^{-1}$ |
|---|---|
| C=C | 1621, 1598 cm$^{-1}$ |
| aromatic | 1568, 1507 cm$^{-1}$ |

EXAMPLE 7

4-[[(2-butyl-4-quinolinyl)-oxy]-methyl]-benzoic acid hydrochloride 0.75 g of the product of Example 6 were introduced into 20 ml of ethanol and after stirring, 2.1 ml of 5N sodium hydroxide were added. The reaction medium was refluxed overnight, then cooled to 0° C. and acidified with concentrated hydrochloric acid. The crystals were filtered off and taken up in 20 ml of ethanol and 15 ml of concentrated sodium hydroxide. The solution was refluxed for 2 hours, then cooled to 0° C., acidified with concentrated hydrochloric acid and stirred for one hour at 0° C. The crystals were washed with water and dried at 90° C. to obtain 0.45 g of the desired product melting at 143° C. After crystallization from 20 ml of ethanol, 0.295 g of the expected product melting at 145° C. were obtained.

Analysis: $C_{21}H_{21}NO_3$; molecular weight=371.81

| | | | | | | | | |
|---|---|---|---|---|---|---|---|---|
| Calculated | % C | 67.82 | % H | 5.9 | % N | 3.76 | % Cl | 9.53 |
| Found: | | 67.5 | | 6.1 | | 3.6 | | 9.2 |

IR Spectrum (Nujol):

| | |
|---|---|
| C=O | 1700 cm$^{-1}$ |
| C=C, C=N, aromatic | 1640, 1612, 1599, 1576, 1536, 1490 cm$^{-1}$ |

EXAMPLE 8

Methyl 4'-[[(2-butyl-4-quinolinyl)-oxy]-methyl](1,1'-biphenyl)-2-carboxylate Using the procedure of Example 6, 0.45 g of the product of Step C of Example 3 in 25 ml of anhydrous acetone and 0.6 g of potassium carbonate and 0.7 g of methyl 4-(bromomethyl)(1.1'-biphenyl)2-carboxylate (prepared according to EP 0,253,310) were reacted to obtain after chromatography on silica (eluant:methylene chloride-methanol 98-2), 0.8 g of the expected product melting at 105° C.

IR Spectrum (CHCl$_3$):

| | |
|---|---|
| COOMe | 1720, 1436 cm$^{-1}$ |
| aromatic, heteroatom | 1620, 1598, 1568, 1507, 1485 cm$^{-1}$ |

EXAMPLE 9

4'-[[(2-butyl-4-quinolinyl)-oxy]-methyl](1,1'-biphenyl)-2-carboxylic acid 0.75 g of the product of Example 8 were introduced into 120 ml of 1N sodium hydroxide and the solution was heated at 90° C. for 5 hours and then 20 ml of ethanol were added. The medium was stirred for one hour at 90° C., then over-night at ambient temperature. The ethanol was evaporated off, and the residue was cooled to 0° C. and acidified with concentrated hydrochloric acid. After stirring for one hour at 0° C., the crystals were separated, washed with water and dried at 50° C. to obtain 0.70 g of product which was crystallized from 150 ml of ethanol to obtain 550 mg of the expected product melting at 145° C.

Analysis: $C_{27}H_{25}NO_3$; molecular weight=411.51

| | | | | | | | |
|---|---|---|---|---|---|---|---|
| Calculated: | % C | 78.8 | % H | 6.12 | % N | 3.4 | |
| Found: | | 78.6 | | 6.12 | | 3.3 | |

IR Spectrum (Nujol):
Absorption OH/NH region

| | |
|---|---|
| =O | 1710 cm$^{-1}$ |
| heterocycle and aromatic | 1599, 1570, 1499 cm$^{-1}$ |

EXAMPLE 10

Ethyl 4-[(2-butyl-4-quinolinyl)-oxy]benzoate 0.950 g of the product of Step D of Example 3 and 2.2 g of ethyl 4-hydroxy benzoate were mixed together and heated to 170° C. for half an hour with stirring. After cooling, the reaction medium was chromatographed on silica (eluant:hexane-ethyl acetate 9-1) to obtain 0.250 g of the expected product.

IR Spectrum (CHCl$_3$):

| | |
|---|---|
| C=O | 1714 cm$^{-1}$ |
| heterocycle and aromatic | 1621, 1609, 1598, 1564, 1498 cm$^{-1}$ |

EXAMPLE 11

4-[(2-butyl-4-quinolinyl)-oxy]-benzoic acid hydrochloride a) 4-[(2-butyl-4-quinolinyl)-oxy]benzoic acid 250 mg of the product of Example 10 were introduced into 6 ml of 2N sodium hydroxide and 5 ml of ethanol and the mixture was heated to 80° C. for one hour. The ethanol was evaporated off and the residue was taken up in water.

b) Preparation of the hydrochloride 2N hydrochloric acid was added to the solution until the pH was 1, followed by filtering, washing with water, drying and crystallizing the product from pentane. The crystals were dried at 60° C. under reduced pressure in the presence of phosphorous pentoxide to obtain 204 mg of the expected product.

Analysis: $C_{20}H_{19}NO_3$; molecular weight=357.84

| | | | | | | | | |
|---|---|---|---|---|---|---|---|---|
| Calculated: | % C | 67.13 | % H | 5.63 | % N | 3.91 | % Cl | 9.91 |
| Found: | | 67.1 | | 5.5 | | 3.8 | | 9.9 |

IR Spectrum (Nujol):

Absorption OH/NH region

| | |
|---|---|
| C=O | 1704 cm$^{-1}$ |
| conjugated system + aromatic | 1644, 1608, 1594, 1538, 1500, 1490 cm$^{-1}$ |

EXAMPLE 12

4-[(2-butyl-4-quinolinyl)-amino]benzoic acid hydrochloride 0.840 g of the product of Step D of Example 3 and 0.640 g of amino benzoic acid were introduced into 15 ml of 1N hydrochloric acid and the solution was refluxed for 3 hours. The precipitate was filtered, washed with water and dried at 60° C. under reduced pressure to obtain 0.830 g of the expected product.

Analysis: $C_{20}H_{20}N_2O_3$ HCl ; molecular weight=356.85

| | | | | | | | | |
|---|---|---|---|---|---|---|---|---|
| Calculated: | % C | 67.32 | % H | 5.93 | % N | 7.85 | % Cl | 9.93 |
| Found: | | 67.1 | | 5.9 | | 7.7 | | 9.6 |

IR Spectrum (Nujol):

Absorption OH/NH region

| | |
|---|---|
| C=O | 1710 cm$^{-1}$ |
| aromatic + heterocycle | 1640, 1613, 1591, 1554, 1517, 1495 cm$^{-1}$ |

EXAMPLE 13

Methyl 4'-[(3-butyl-4-cinnolinyl)-methyl](1,1'-bipheny)-2-carboxylate

STEP A: 2-(1-hexynyl)benzeneamine

32 mg of copper iodide and 140 mg of bistriphenyl phosphine palladium chloride and 2.3 ml of 1-hexyne were added to a solution of 4.4 g of 2-iodo aniline in 100 ml of triethylamine and the mixture was stirred for 15 hours at ambient temperature, then evaporated to dryness. The residue was taken up in ether and the insoluble part was filtered out, washed with ether and the ethereal fractions were evaporated to dryness. The residue was chromatographed on silica (eluant:hexane-ethyl acetate (9-1)) to obtain 3.27 of the desired product.

IR Spectrum

| | |
|---|---|
| $C_6H_4$—$NH_2$ | 3486 cm$^{-1}$ |
| $NH_2$ def + aromatic | 1613, 1570, 1493 cm$^{-1}$ |

STEP B: 3-butyl-4-hydroxy cinnoline

A solution of 2 g of sodium nitrite in 60 ml of water was added at 0° C. to a suspension at 0° C. of 3.2 g of the product of Step A in 100 ml of concentrated hydrochloric acid, and the mixture was stirred for 90 minutes at 0° C., then for one hour at 100° C. The reaction medium was poured into 100 ml of ice-cooled water, separated and washed with ice-cooled water. The moist product was taken up in 100 ml of water and alkalized with concentrated ammonium hydroxide. After separation, the residue was washed with water and dried at 70° C. under reduced pressure to obtain 1.47 g of the expected product melting at 180° C.

IR Spectrum (Nujol):

| Absorption OH/NH region | |
|---|---|
| C=C + Aromatic | 1636 cm$^{-1}$ |
| | 1064 cm$^{-1}$ (shoulder) |
| | 1580 cm$^{-1}$ |
| | 1578 cm$^{-1}$ |
| | 1498 cm$^{-1}$ |

STEP C: 3-butyl-4-chloro-cinnoline

Using the procedure of Step F of Example 1, 1.2 g of the product of Step B and 10 ml of phosphorous oxychloride were reacted to obtain after chromatography on silica (eluant:hexane-ethyl acetate (6.4)), 1.16 g of the desired product melting at <50° C.

IR Spectrum (CHCl$_3$):

| | |
|---|---|
| C=C + aromatic | 1616, 1558 cm$^{-1}$ |

STEP D

Using the procedure of Example 1, 1.1 g of product of Step C, 1.83 g of methyl 4-(bromomethyl)(1,1'-biphenyl)-2-carboxylate (prepared according to EP 0,253,310), 0.4 g of ethanolic zinc, 700 mg of tetrakis(triphenyl-phosphine) palladium in 100 ml of tetrahydrofuran were reacted. The reaction medium was placed under ultrasonics for 15 hours, then taken up in water and extracted with ethyl acetate. The organic phase was washed with water, dried and evaporated. After chromatographing on silica (eluant:methylene chloride-acetonitrile 8-2), 760 mg of the expected product were obtained.

IR Spectrum (CHCl$_3$):

| | |
|---|---|
| C=O | 1720 cm$^{-1}$ |
| conjugated sytem + Aromatic | 1614, 1599, 1567, 1535, 1515 cm$^{-1}$ |

EXAMPLE 14

4'[(3-butyl-4-cinnolinyl)-methyl](1,1'-biphenyl)-2-carboxylic acid

Using the procedure of Example 2, 700 mg of the product of Example 13 in 10 ml of 2N sodium hydroxide and 20 ml of ethanol and the reaction medium was refluxed for 2 hours, poured into water and acidified by the addition of concentrated hydrochloric acid. The precipitate was washed with water, dried under reduced pressure and crystallized from 20 ml of acetonitrile to obtain 0.27 g of the expected product melting at 210° C.

Analysis: $C_{26}H_{24}N_2O_3$ HCl; molecular weight=396.489

| | | % C | | % H | | % N | |
|---|---|---|---|---|---|---|---|
| Calculated: | | 78.76 | | 6.1 | | 7.06 | |
| Found: | | 78.6 | | 6.0 | | 7.1 | |

IR Spectrum (Nujol):

| Absorption OH/NH region | |
|---|---|
| C=O | 1718 cm$^{-1}$ |
| conjugated system + aromatic | 1622, 1598, 1576, 1558, 1522 cm$^{-1}$ |

EXAMPLE 15

4-[[(3-butyl-4-cinnolinyl)-oxy]-methyl]benzonitrile

Using the procedure of Example 6, the product of Step B of Example 13 and 4-(bromomethyl)benzonitrile were reacted to obtain the desired product.

EXAMPLE 16

4-[[(3-butyl-4-cinnolinyl)-oxy]-methyl]benzoic acid

Using the procedure of Example 7, the product of Example 15 was reacted to obtain the desired product.

EXAMPLE 17

Methyl 4'-[[(3-butyl-5-methylthio-4-quinolinyl)-oxy]-methyl](1,1'-biphenyl)-2-carboxylate

STEP A: Diethyl 2-butyl-3-[[3-(methylthio)-phenyl]-amino]-2-butenedioate

50 mg of p-toluene sulfonic acid were added to a solution of 4.3 g of diethyl 2-butyl-3-oxo butanedioate with 2 ml of 3-(methylthio)aniline in 100 ml of toluene and the mixture was stirred for 4 hours at reflux while eliminating the water formed. After evaporation to dryness, the residue was chromatographed on silica (eluant:methylene chloride with 30% hexane) to obtain 5.1 g of the desired product melting at 55° C.

IR Spectrum (CHCl$_3$):

| =C—NH complex | 3240 cm$^{-1}$ |
| C=O | 1732–1658 cm$^{-1}$ |
| C=c + aromatic | 1598, 1583, 1488 cm$^{-1}$ |

Preparation of diethyl 2-butyl-3-oxo butanedioate 100 ml of ether, then 13.55 ml of diethyl oxalate were added to a solution of sodium ethylate, prepared by stirring 2.3 g of sodium and 150 ml of ethanol, for one hour at 40° C. and the mixture was refluxed for 15 minutes, cooled slightly and 50 ml of ethyl caproate were added. The mixture was stirred for 3 hours at reflux and for 16 hours at 30° C. to 35° C. 50 ml of water were added and the aqueous phase was separated by decanting, washed twice with ether and acidified with 2N hydrochloric acid. Extraction was carried out 3 times with ether and the organic phases were washed with water, then with a saturated solution of sodium chloride, dried and evaporated to dryness. The 9.5 g of the desired product were used as is for the following step.

STEP B: Ethyl 3-butyl-1,4-dihydro-5-(methylthio)-4-oxo-2-quinoline carboxylate 1 g of the product of Step A was heated at 250° C. for 45 minutes and then was cooled. The crude reaction product was chromatographed on silica (eluant:methylene chloride) to obtain 700 mg of the desired product melting at 80° C.

IR Spectrum (CHCl$_3$):

| NH Complex | 3330 cm$^{-1}$ (F) |
| | 1743 cm$^{-1}$, 1707 (f) |
| C=O | 1610, 1596, 1559, 1530 cm$^{-1}$ |
| C=O + C=C aromatic | |

STEP C: 3-butyl-1,4-dihydro-5-(methylthio)-4-oxo-2-quinolinecarboxylic acid hydrochloride 0.63 g of the product of Step B in 10 ml of N sodium hydroxide solution was stirred for 2 hours at reflux and the mixture was then poured into ice-cooled water. The mixture was acidified with concentrated hydrochloric acid, separated, washed with water, dried and impasted in 100 ml of ethyl acetate to obtain 495 mg of the desired product melting at 140° C.

IR Spectrum (Nujol):

| Absorption OH/NH | 3328 CM$^{-1}$ |
| C=O | 1744 cm$^{-1}$ |
| C=O + C=C aromatic | 1610, 1592, 1560, 1540, 1516 cm$^{-1}$ |

STEP D: 3-butyl-5-(methylthio)-4(1H)-quinolone 390 mg of the product of Step C were heated at 260° C. for 5 minutes to obtain 300 mg of the desired product melting at 144° C.

IR Spectrum (CHCl$_3$):

| =C—NH | 3365 cm$^{-1}$ |
| C=O + C=C aromatic | 1627, 1609, 1585, 1560, 1520 cm$^{-1}$ |

STEP E:

A solution of 1.1 g of the product of Step D and 1.63 g of methyl 4-(bromomethyl)(1,1'-biphenyl)-2-carboxylate (prepared according to EP 0,253,310) in 50 ml of acetone with stirring was prepared, and 1.2 g of potassium bicarbonate were added. The reaction medium was refluxed for 2 hours and the suspension was separated. The insoluble part was washed with acetone, filtered and dried. After chromatography on silica (eluant:ethyl acetate-hexane 5-5), 1.8 g of the expected product were obtained.

IR Spectrum (CHCl

| C=OMe ‖ O | 1720, 1435 cm$^{-1}$ |
| aromatic + $^1$heteroatom | 1600, 1593, 1557, 1505, 1483 cm$^{-1}$ |

EXAMPLE 18

Diethylamine salt of 4'-[[(3-butyl-1,4-dihydro-5-(methylthio)-4-quinolinyl)-oxy]-methyl](1,1'-biphenyl)-2-carboxylic acid A mixture of 1.8 g of the product of Example 17 with 20 ml of a solution of 5N sodium hydroxide in 20 ml of ethanol was stirred for 2 hours at reflux and the mixture was poured into water and acidified with sodium hydrogen phosphate. The mixture was extracted with ethyl acetate and the extracts were washed with water, dried and evaporated to dryness. The residue was chromatographed on silica (eluant:methylene chloride-methanol (9-1)) and the product was dissolved in 50 ml of ethyl acetate. 0.15 ml of diethylamine was added and the mixture was stirred for 30 minutes. After separating and washing twice with 10 ml of ethyl acetate, then with 50 ml of isopropyl ether, the residue was dried at ambient temperature to obtain 3809 mg of the expected product melting at 160° C.

Analysis: $C_{32}H_{38}N_2O_3S$; molecular weight=530.735

| | % C | % H | % N | % S |
|---|---|---|---|---|
| Calculated: | 72.42 | 7.22 | 5.28 | 6.04 |
| Found: | 71.6 | 7.1 | 5.1 | 5.9 |

IR Spectrum (CHCl$_3$):

$NH_2^{\oplus}$ and/or —N—H$^{\oplus}$—H type absorption approx. 3100, 2200 cm$^{-1}$

| C=O | 1624, 1592, 1558, 1516 cm$^{-1}$ |

EXAMPLE 19

Ethyl 3-butyl-4-[[2'-methoxycarbonyl)(1,1'-biphenyl)-4-yl]-methoxy]-2-quinoline carboxylate Using the procedure of Example 8, 0.2 g of the product of Step C of Example 1 in 5 ml of anhydrous acetone and 0.2 g of potassium carbonate were reacted. After stirring, 0.21 g of methyl 4-(bromomethyl)(1,1'-biphenyl)-2-carboxylate (prepared according to EP 0,253,310) were added and after chromatography on silica (eluant:methylene chloride-methanol 99-1), 180 mg of the expected product were obtained.

IR Spectrum (CHCl$_3$):

| =O | 3100–2200 cm$^{-1}$ |
| conjugated system + aromatic | 1618 1599, 1584, 1562, 1492 cm$^{-1}$ |

EXAMPLE 20

3-butyl-4-[[2'-carboxy-(1,1'-biphenyl)-4-yl]-methoxy-2-quinolinecarboxylic acid Using the procedure of Example 9, 0.3 g of the product of Example 19 in 5 ml of concentrated sodium hydroxide were reacted. 2 ml of water and 5 ml of ethanol were added the mixture was refluxed for 3 hours. The ethanol was evaporated off and the solution was cooled to 0° C. and acidified with hydrochloric acid. The crystals were separated out, washed with water and dried. After crystallization from 10 ml of dimethylformamide with about 1% water, 0.176 g of the expected product melting at 162 were obtained.

Analysis: $C_{28}H_{25}NO_5$; molecular weight=455.52

| Calculated: | % C | 73.12 | % H | 5.68 | % N | 3.16 |
|---|---|---|---|---|---|---|
| Found: | | 72.8 | | 5.7 | | 3.1 |

IR Spectrum (Nujol):

| =O | 17110, 1672 $cm^{-1}$ |
|---|---|
| aromatic + heteroatom | 1645, 1615, 163, 1522, 1485 $cm^{-1}$ |

EXAMPLE 21

4'[[(3-butyl-4-quinolinyl)-oxy]-methyl](1,1'-biphenyl)-2-carboxylic acid

The desired product was obtained from the product of Example 210 by decarboxylation in biphenyl oxide by heating at 250° C. for 5 minutes.

EXAMPLE 22

Methyl 4'-{(2-phenyl-4-quinazolinyl)-methyl](1,1'-biphenyl)-2-carboxylate

[[2'-(methoxycarbonyl)(1,1'-biphenyl)-4-yl]-methyl]zinc bromide was prepared in advance from 400 mg of zinc in 1 ml of tetrahydrofuran and 1.53 g of methyl 4-(bromomethyl)(1,1'-biphenyl)-2-carboxylate (KNOCHEL, J. Org. Chem., 1988, Vo. 53, p. 5789 to 5791) and 240.69 mg of 4-chloro-2-phenyl-quinazoline and 115 mg of palladium tetrakis (triphenyl-phosphine) complex were added to the solution. The mixture stood at 50° C. for 6 hours and the reaction medium was poured into a water/ice/acetic acid mixture. The aqueous phase was extracted with ethyl acetate and the organic phase was washed with water and water saturated with sodium chloride, dried and evaporated. After chromatography on silica (eluant:ethyl acetate-hexane 1-9 then 2-8), 260 mg of expected product melting at 120° C. to 121° C. after crystallization from isopropyl ether were obtained.

IR Spectrum (CHCl$_3$):

| C=O | 1722 $cm^{-1}$ |
|---|---|
| aromatic + | 1618, 1600, 1534, 1520, 1459 $cm^{-1}$ |

EXAMPLE 23

4'-[(2-phenyl-4-quinazolinyl)-methyl](1,1'-biphenyl)-2-carboxylic acid 240 mg of the product of Example 22 were introduced into 2 ml of ethanol and 0155 ml of 2N sodium hydroxide were added. The solution was stirred for 2 days at ambient temperature and then was refluxed for 2 hours. The solution was evaporated to dryness and the residue was taken up in water and neutralized with concentrated hydrochloric acid. The precipiate was filtered, dried and crystallized from a water-isopropyl alcohol mixture 10-90 to obtain 150 mg of the expected product melting at 210° C.

Analysis: $C_{28}H_{20}N_2O_2$; molecular weight=416.48

| Calculated: | % C | 80.75 | % H | 4.84 | % N | 6.72 |
|---|---|---|---|---|---|---|
| Found: | | 80.7 | | 4.9 | | 6.7 |

IR Spectrum (Nujol):

| C=O | 1698 $cm^{-1}$ |
|---|---|
| aromatic | 1618, 1600, 1572, 1548, 1518, 1498 $cm^{-1}$ |

EXAMPLE 24

Methyl 4'-[(2-butyl-4-quinazolinyl)-methyl](1,1'-biphenyl)-2-carboxylate

STEP A: N(2(cyanophenyl)valeramide)

10 g of orthocyanoaniline were dissolved in 50 ml of anhydrous pyridine and after 11.2 ml of valeroyl chloride were added, the mixture was refluxed for 2 hours. The reaction mixture was poured into 100 ml of ice-cooled water and acidified with aqueous 2N HCl until pH=7. Extraction was carried out with ethyl acetate and the combined organic phase were washed first with 100 ml of water and then with 100 ml of a saturated soluton of sodium chloride. The organic phase was dehydrated over anhydrous magnesium sulfate, filtered and evaporated. The solid was impasted in isopropyl ether, followed by filtering and evaporating to obtain 13.7 g of the expected product melting at 76° C.

IR Spectrum (CHCl$_3$):

| —NH | 3416 $cm^{-1}$ |
|---|---|
| —c=N | 2222 $cm^{-1}$ |
| aromatic + amide | 1605, 1583, 1520 $cm^{-1}$ |

STEP B: 2-butyl-4-oxo-quinazoline 13.7 g of the product of Step A were dissolved in 150 ml of dioxane and 400 ml of an aqueous sodium hydroxide solution and then 18 ml of 30% hydrogen peroxide were added. The mixture was refluxed for 2 hours and acetic acid was added until the pH=3. Then, 28% ammonium hydroxide was added until the pH=8 in an ice bath. Filtration was carried out, followed by washing with water and drying under reduced pressure at 50° C. to obtain 10.56 g of the expected product melting at 156° C.

IR Spectrum (CHCl$_3$):

| NH / NH | 3385 $cm^{-1}$ |
|---|---|
| >=O | 1674 $cm^{-1}$ |
| aromatic | 1613, 1565 $cm^{-1}$ |

STEP C: 2-butyl-4-chloro quinazolone 100 mg of the product of Step B were introduced with magnetic stirring at 0° C. into 1 ml of phosphorous oxychloride and then 85 microliters of N,N-diisopropylethylamine were added. The mixture was allowed to return to ambient temperature, refluxed for 2 hours and then allowed to return to ambient temperature. The mixture was evaporated to dryness and then dissolved in a minimum of methylene chloride, washed with water and water saturated in sodium chloride. Extraction was carried out with ethyl acetate and the extracts were dried over magnesium sulfate, filtered and evaporated to dryness. The residue was purified on silica (eluant:methylene chloride-ethyl acetate 95-5) to obtain 28 mg of the expected product which was used as is for the next step.

STEP D: Methyl 4'-[(2-butyl-4-quinazolinyl)-methyl](1,1'-biphenyl)-2-carboxylate Using the procedure of Example 22, 4-chloro-2-butyl quinazoline of Step C and organic also prepared as indicated in Example 22 were reacted to obtain the expected product.

EXAMPLE 25

4'-[(2-butyl-4-quinazolinyl)-methyl](1,1'-biphenyl)-2-carboxylic acid

Using the procedure of Example 23, the product of Example 24 were reacted to obtained the desired product.

EXAMPLE 26

Methyl 4'-[[[3-butyl-2-(hydroxymethyl)-4-quinolinyl]-oxy]-methyl](1,1'-biphenyl)-2-carboxylate Using the procedure of Example 23, the desired product was obtained.

EXAMPLE 27

4'-[[[3-butyl-2-(hydroxymethyl)-4-quinolinyl]-oxy]-methyl](1,1'-biphenyl)-2-carboxylic acid Using the procedure of Example 23, the product of Example 26 was reacted to obtain the desired product melting at 174° C.

EXAMPLE 28

Methyl 4-[2-[(2-butyl-4-quinolinyl)-oxy]-ethyl]-benzoate

Using the procedure of Example 23, the desired product was obtained.

EXAMPLE 29

4-[2-[(2-butyl-4-quinolinyl)oxy]-ethyl]-benzoic acid

Using the procedure of Example 23, the product of Example 28 was reacted to obtain the desired product melting at 205° C.

EXAMPLE 30

Methyl 4'-[(3-butyl-1,4,5,6,7,8-hexahydro-4-quinolinyloxy)-methyl](1,1'-biphenyl)-2-carboxylate
STEP A: 3-butyl-1,4,5,6,7,8-hexahydro-4-oxo-1-quinoline 1 g of the product of Step a) was introduced into 60 ml of methanol and about 10 mg of platinum oxide were added. The mixture was hydrogenated under a pressure of about 200 mBar and after about 3 hours of stirring at ambient temperature, the solution was filtered and evaporated. After chromatography (eluant:methylene chloride-methanol 98-2), 0.6 g of the expected product melting at 220° C. were obtained.

IR Spectrum in chloroform

| =C—N—H | 3430 cm$^{-1}$ |
|---|---|
| >=O | 1632 cm$^{-1}$ |
| conjugated systems | 1538 cm$^{-1}$, 1510 cm$^{-1}$ |

STEP B: Methyl 4'-[[(3-butyl-1,4,5,6,7,8-hexahydro-4-quinolinyl-oxy]-methyl](1,1 '-biphenyl)-2-carboxylate (Product B) and Methyl 4'-[(3-butyl-1,4,5,6,7,8-hexahydro-4-oxo-1-quinolinyl)-methyl](1,1'-biphenyl)-2-carboxylate (Product A)

0.4 g of the product of Step A were introduced into 10 ml of anhydrous acetone and 0.52 g of potassium carbonate and 0.6 g of methyl bromomethyl (1,1'-biphenyl)-2-carboxylate were added. The mixture was refluxed over-night and then the reaction medium was poured into 100 ml of water. The aqueous phase was extracted with 50 ml of ethyl acetate three times and the organic phase was dried and evaporated to dryness. After chromatography (eluant:methylene chloride-methanol 98-2), 0.15 g of the expected product B as well as 0.45 g of the product A were obtained.

IR Spectrum of product A in chloroform

| >=O | 1726 cm$^{-1}$ |
|---|---|
| C=C | 1636 cm$^{-1}$ |
| aromatic | 1595 cm$^{-1}$ |
| C=O | 1547 cm$^{-1}$ |
| | 1495 cm$^{-1}$ |

IR Spectrum of product B in chloroform

| >=O | 1720 cm$^{-1}$ |
|---|---|
| aromatic | 1617 cm$^{-1}$, 1600 cm$^{-1}$, 1589 cm$^{-1}$, 1519 cm$^{-1}$ |
| | 1482 cm$^{-1}$ |

EXAMPLE 31

4'-[((3-butyl-1,4,5,6,7,8-hexahydro-4-quinolinyl)-oxy)-methyl](1,1'-biphenyl)-2-carboxylic acid and 4'-[(3-butyl-1,4,5,6,7,8-hexahydro-4-oxo-1-quinolinyl-methyl)(1,1'-biphenyl)-2-carboxylic acid a) 4'-[(3-butyl-1,4,5,6,7,8-hexahydro-4-oxo-1-quinolinyl-methyl)(1,1'-biphenyl)-2-carboxylic acid.

0.43 g of product A of Example 30 were introduced into 10 ml of a normal sodium hydroxide solution and the mixture was heated for one hour at 60° C. After stirring for about one hour, 1 ml of ethanol was added and the mixture was stirred over-night at about 40° C. After cooling to ambient temperature, glacial acetic acid was added until the acid crystallized. After stirring for about one hour, the medium was separated, washed with water, then with ether. Crystallization was carried out from 80 ml of ethanol to obtain 0.310 g of expected product melting at 260° C.

IR Spectrum in (Nujol):

| >=O | 1672 cm$^{-1}$ |
|---|---|
| conjugated system C=O | 1630 cm$^{-1}$ |
| C=O | 1600 cm$^{-1}$ |
| aromatic | 1535 cm$^{-1}$ |
| | 1520 cm$^{-1}$ | b) 4'-[((3-butyl-1,4,5,6,7,8-hexahydro-4-quinolinyl)-oxy)-methyl](1,1'-biphenyl)-2-carboxylic acid.

Starting with product B of Example 30, and using the same conditions as in a) the expected product was obtained.

EXAMPLE 32

Methyl 4'-[(3-butyl-1,4,5,6,7,8-hexahydro-6-methyl-4-quinolinyl)-methyl](1,1'-biphenyl)-2-carboxylate (product B) and methyl 4'-[(3-butyl-1,4,5,6,7,8-hexahydro-6-methyl-4-oxo-1-quinolinyl)-methyl](1,1'-biphenyl)-2-carboxylate (product A)

STEP A: 2-ethyl-6-methyl 3-butyl-4-hydroxy-2,6-quinoline dicarboxylate a) Diethyl 2-butyl-3-[(4-methoxycarbonyl)-phenyl)-amino]-2-butenedioate 27.8 g of methyl 4-aminobenzoate and 47 g of diethyl 2-butyl-3-oxo butenedioate were admixed and 2 g of activated siliporite were added. The mixture was stirred for about 30 hours at 60° C. and after chromatography (eluant:hexane-ethyl acetate 95-5), 70 g of the expected product were obtained.

The 70 g of product obtained in a) were mixed with 70 ml of DOWTHERM and the mixture was heated at about 250° C. for about 30 minutes, cooled, impasted in ether and separated to obtain 45 g of the expected product melting at 160° C.

IR Spectrum in chloroform

| =C—NH— | 3422 cm$^{-1}$, 3380 cm$^{-1}$ |
|---|---|
| >=O | 1742 cm$^{-1}$, 1715 cm$^{-1}$, 1631 cm$^{-1}$ |
| aromatic | 1603 cm$^{-1}$ |
| C=C | 1577 cm$^{-1}$ |
|  | 1525 cm$^{-1}$ |

STEP B: 3-butyl-4-hydroxy-6-quinoline carboxylic acid a) 3-butyl-1,4-dihydro-4-hydroxy-2,6-quinoline dicarboxylic acid 40 g of the product of Step F were introduced into 150 ml of concentrated sodium hydroxide and 15 ml of ethanol were added. The mixture was heated for about 4 hours at about 80° C. and 100 ml of an ice and water mixture were added. The mixture was acidified with concentrated hydrochloric acid, then separated, washed with water and dried to obtain 24 g of the expected product melting at >260° C.

b) 3-butyl-4-hydroxy-6-quinoline carboxylic acid 24 g of the product of a) were introduced into 350 ml of DOWNTHERM and the mixture was heated at about 250° C. for 5 hours, cooled to ambient temperature, impasted in ether, separated, washed with water and dried to obtain 17.8 g of the expected product melting at 260° C.

IR Spectrum in Nujol:

| >=O | 1702 cm$^{-1}$, 1682 cm$^{-1}$, 1640 cm$^{-1}$ |
|---|---|
| C=C | 1616 cm$^{-1}$ |
| aromatic | 1597 cm$^{-1}$, 1568 cm$^{-1}$, 1492 cm$^{-1}$ |

STEP C: 3-butyl-6-hydroxymethyl-4-(1H)-quinolinone 3 g of the product of Step B were introduced into 800 ml of tetrahydrofuran and 1.8 g of lithium-aluminum tetrahydride were added. The mixture was stirred for about 5 hours at ambient temperature and after about 5 ml of a THF/water solution (80-20) were added, a saturated solution of double tartrate salt was added slowly, followed by filtering. The precipitate was washed with tetrahydrofuran and dried to obtain 2.5 g of the expected product melting at 260° C.

IR Spectrum in Nujol:

| C=O | 1638 cm$^{-1}$ |
|---|---|
| conjugated system | 1620 cm$^{-1}$ |
| aromatic | 1568 cm$^{-1}$ |
|  | 1550 cm$^{-1}$ |
|  | 1508 cm$^{-1}$ |
|  | 1490 cm$^{-1}$ |

STEP D: 3-butyl-1,4,5,6,7,8-hexahydro-6-methyl-4-(1H) quinolinone①  and 3-butyl-1,4,5,6,7,8-hexahydro-6-hydroxymethyl- 4-(1H)quinolinone②

0.5 g of the product of Step C was introduced into 100 ml of methanol and after 10 mg of platinum oxide were added, the mixture was hydrogenated under approximately 300 mBar for about 24 hours. Filtration was carried out, followed by washing with methanol and drying. After chromatography (eluant:methylene chloride-methanol 95-5), 0.47 g of the expected product [1] were obtained which melted at approx. 260° C.

IR Spectrum in Nujol of [1]

| >=O | 1632 cm$^{-1}$ |
|---|---|
| conjugated system | 1603 cm$^{-1}$ |
| C=C | 1500 cm$^{-1}$ |
| C—N |  |

STEP E: Methyl 4'-[((3-butyl-1,4,5,6,7,8,-hexahydro-6-methyl-4-quinolinyl)-oxy)-methyl](1,1'-biphenyl)-2-carboxylate (product B) and methyl 4'-[(3-butyl-1,4,5,6,7,8-hexahydro-6-methyl-4-oxo-1-quinolinyl)-methyl(1,1'-biphenyl)-2-carboxylate (product A)

Using the procedure of Example 30, 0.45 g of product [1] of Step D in 20 ml of anhydrous acetone, 0.55 g of potassium carbonate and 0.61 g of methyl bromomethyl (1,1'-biphenyl)-2-carboxylate were added and the mixture was refluxed for about 3 hours. The reaction medium was poured into 100 ml of water and the aqueous phase was extracted with 50 ml of ethyl acetate. The organic phase was dried and evaporated and after chromatography (eluant:methylene chloride-methanol 95-5), 0.1 g of product B as well as 0.58 g of product A were obtained.

IR Spectrum in chloroform of product A

| —C—OMe<br>‖<br>O | 1725 cm$^{-1}$<br>1434 cm$^{-1}$ |
|---|---|
| C=O | 1638 cm$^{-1}$ |
| C=O | 1600 cm$^{-1}$ |
| aromatics | 1545 cm$^{-1}$, 1594 cm$^{-1}$ |

EXAMPLE 33

4'-[((3-butyl-1,4,5,6,7,8-hexahydro-6-methyl-4-quinolinyl)-oxy)-methyl](1,1'-biphenyl)-1-carboxylic acid and 4-'((3-butyl-1,4,5,6,7,8-hexahydro-6-methyl-4-oxo-1-quinolinyl)-methyl)(1,1'-biphenyl)-2-carboxylic acid a) 4'-[(3-butyl-1,4,5,6,7,8-hexahydro-6-methyl-4-oxo-1-quinolinyl)-methyl](1,1'-biphenyl)-2-carboxylic acid Using the procedure of Example 31, 0.4 g of product A of Example 32 in 10 ml of 2N sodium hydroxide were reacted. The mixture was stirred over-night at about 60° C. and the medium was cooled to ambient temperature, acidified with glacial acetic acid, decanted, impasted in a solution of 2N hydrochloric acid, separated, dried and crystallized from 50 ml of an ethanol-water 49-1 mixture to obtain 0.220 g of the expected product melting at 255° C.

IR Spectrum in Nujol

| >=O | 1675 cm$^{-1}$, 1628 cm$^{-1}$ |
|---|---|
| C=C | 1600 cm$^{-1}$ |
| aromatic | 1533 cm$^{-1}$ |
|  | 1517 cm$^{-1}$ | b) 4'-[((3-butyl-1,4,5,6,7,8-hexahydro-6-methyl-4-quinolinyl)-oxy)-methyl](1,1'-biphenyl)-2-carboxylic acid Starting with product B of Example 32 and proceeding under the same conditions as in a), the product A of Example 32 was reacted to obtain the expected product.

Starting with product 2 of Step D of Example 32 and by proceeding in the same manner as Step E of Example 32 starting with product 1 of this Step D, the following products were obtained:

B$_1$: methyl 4'-[((3-butyl-1,4,5,6,7,8-hexahydro-6-hydroxymethyl-4-quinolinyl)-oxy)-methyl](1,1'-biphenyl)-2-carboxylate and A$_1$: methyl 4'-[(3-butyl-1,4,5,6,7,8-hexahydro-6-hydroxymethyl-4-oxo-1-quinolinyl)-methyl)(1,1'-biphenyl)-2-carboxylate.

Starting with products A$_1$ and B$_1$ and using the procedure of Example 33, the following acids were obtained starting respectively with A$_1$:
4'-((3-butyl-1,4,5,6,7,8-hexahydro-6-hydroxymethyl-4-oxo-1-quinolinyl)-methyl)(1,1'-biphenyl)-2-carboxylic acid and with B$_1$:
4'-[((4-butyl-1,4,5,6,7,8-hexahydro-6-hydroxymethyl-4-quinolinyl)-oxy)-methyl](1,1'-biphenyl)-2-carboxylic acid.

EXAMPLE 34

Methyl carboxylate of the carboxylic acid of Example 35

EXAMPLE 35

4'-(((2-(2-methylproyl)-8-(trifluoromethyl)-4-quinolinyl)-oxy)-methyl)(1,1'-biphenyl)-2-carboxylic acid Characterized by its melting point of 164° C., the product of Example 34 was prepared as indicated above for the preceding examples starting with methyl carboxylate (position 2' of the biphenyl) which constitutes Example 34, itself prepared as indicated above for the preceding examples.

The above products can also be obtained under the conditions described above and represent Examples 36 and 37:

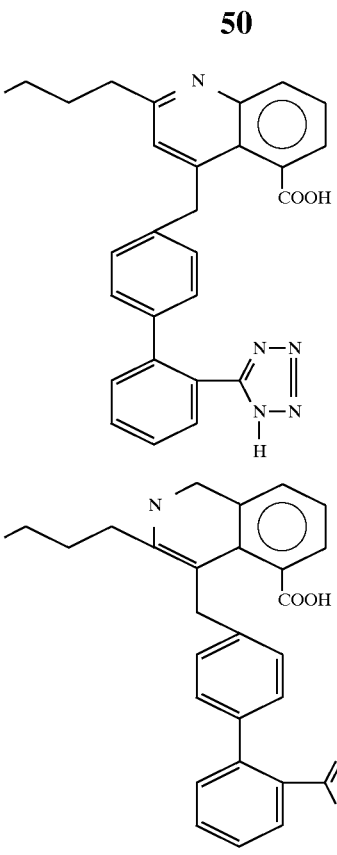

EXAMPLE 38
Pharmaceutical composition

Tablets were prepared containing 10 mg of the product of Example 4 and sufficient excipient of lactose, talc, starch and magnesium stearate for a final tablet weight of 100 mg.

PHARMACOLOGICAL RESULTS

1) Test on the angiotensin II receptor

A fresh membrane preparation obtained from the liver of a rat was used. The tissue was ground up in a polytron in a Tris 50 mM pH 7.4 buffer and after being ground up, the tissue was centrifuged 3 times at 30,000 g for 15 mintues with intermediate taking up of the deposits in the Tris pH 7.4 buffer. The last deposits were suspended in a pH 7.4 incubation buffer (Tris 20 mM, NaCl 135 mM, KCl 10 mM, glucose 5 mM, MgCl$_2$ 10 mM, benzyl sulfonyl fluoride 0.3 mM, bacitracin 0.1 mM, (0.2% bovine albumin serum). 2 ml aliquoted fractions were divided into hemolysis tubes and 125$_I$ angiotensin II (25,000 DPM/tube) and the product to be studied were added. The product was first tested at 3×10$^{-5}$M in triplicate. When the test product displaced more than 50% of the radioactivity linked specifically to the receptor, it was tested again in a range of 7 concentrations to determine the concentration that inhibited the radioactivity linked specifically to the receptor by 50%. In this way, the 50% inhibiting concentration was determined.

The non-specific bond was determined by the addition of the product of Example 94 of the European Patent No. 0,253,310 at 10$^{-5}$M (in triplicate). The deposit was incubated at 25° C. for 150 minutes, put back on a water bath at 0° C. for 5 minutes, filtered under vacuum, rinsed with Tris pH 7.4 buffer and the radioactivity was counted in the presence of scintillating Triton. The results were expressed directly as a 50% inhibiting concentration (IC$_{50}$), that is to say as a concentration of product studied, expressed in nM, necessary to displace 50% of the specific radioactivity fixed on the receptor studied.

Results

| Product of Example | IC$_{50}$ in nanomoles |
|---|---|
| 4 | 540 |

2) Revealing the antagonistic activity of angiotensin II on the isolated portal vein The portal vein was removed from male Wistar rats weighing about 350 g (IFFA Credo France) after cervical dislocation. It was put rapidly into a physiological solution (see below) at ambient temperature and a ring of about 1 mm was mounted in a bath with an isolated element containing 20 ml of the following physiological solution (composition in mM: NaCl 118.3-KCl 4.7-MgSO$_4$ 1.2-KH$_2$PO$_4$ 1.2-NaHCO$_3$ 25-glucose 11.1-CaCl$_2$ 2.5). The medium was held at 37° C. and oxygenated by a mixture of O$_2$ 95%, CO$_2$ 5%. The initial pressure imposed was 1 g and the rings were left at rest for 60 to 90 minutes. To avoid spontaneous contractions, verapamil was added to the incubation bath ($1.10^{-6}$M).

At the end of rest period, angiotensin II (Ciba hypertensin) $3.10^{-8}$M was added to the incubation bath and left in contact with the preparation for one minute. This operation was repeated every 30 minutes with the tissue being washed 3 or 4 times between two stimulations with angiotensin. The compound to be studied was introduced into the bath 15 minutes before a new stimulation with angiotensin. As increasing concentrations of this molecule were used, an IC$_{50}$ (concentration that produced a 50% inhibition of the response to angiotensin) was calculated, expressed in nanomoles.

Results

| Product of Example | IC$_{50}$ in nanomoles |
|---|---|
| 4 | 131 |

3) Study of the activity on the endotheline receptor

A membrane preparaton was prepared from rat's posteror cortex plus cerebellum. The tissue was ground up in a POLYTRON in a Tris buffer 50 mM pH=7.4. After 30 minutes at 25° C. (W.B.), the homogenate was centrifuged at 30,000 g for 15 minutes (2 centrifugings with intermediate taking up in the Tris buffer pH 7.4). The deposits were suspended in an incubation buffer (Tris 25 mM, pepsteatine 5 microg/ml, aprotinine 3 microg/ml. PMSF 0.1 mM, EDTA 3 mM, EGTA 1 mM pH 7.4). 2 ml aliquots were distributed in hemolysis tubes and 125$_I$ Endotheline (about 50,000 dpm/tube) and the product to be studied were added. The product was first tested at $3 \times 10^{-5}$M in triplicate. When the tested product displaced by more than 50% the radioactivity linked specifically to the receptor, it was tested again in a range of 7 concentrations to determine the concentration that inhibited the radioactivity linked specifically to the receptor by 50%. In this way, the 50% inhibiting concentration was determined.

The non-specific bond was determined by the addition of endotheline at $10^{-6}$M (in triplicate). The aliquot was incubated at 25° C. for 60 minutes, put in a water bath at 0° C. for 5 minutes, filtered under reduced pressure, rinsed with Tris buffer 7.4 pH and the radioactivity was counted in the presence of scintillating Triton. The result was expressed directly as a 50% inhibiting concentration (IC$_{50}$), that is to say as a concentration of product studied expressed in nM, necessary to displace by 50% the specific radioactivity fixed to the receptor studied. The IC$_{50}$ found the product of Example 35 was 14,000 nanomoles.

4) Investigation of an antagonistic activity of the vasoconstrictive effect of endotheline in a demedullated rat The vasoconstriction caused by injections (IV) of cumulative doses of endotheline (1-3-10-30 μg/kg) was measured by the increase of average arterial pressure in a control group of rats (Sprague Dawley), anaesthetized, then demedullated. The products to be tested were injected 10 minutes before the range of concentrations of endotheline and the decrease in response to endotheline indicated an antagonistic effect. The product of Example 35 showed an antagonistic effect with 1 mg/kg (IV).

Various modifications of the products and method of the invention may be made without departing from the spirit or scope thereof and it should be understood that the invention is only intended to be limited as in the appended claims.

What is claimed is:

1. A compound selected from the group consisting of all possible racemic, enantiomeric and diasteroisomeric forms of a compound of the formula

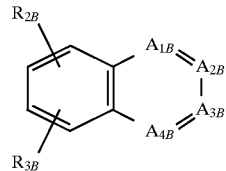

wherein R$_{2B}$ and R$_{3B}$ are individually selected from the group consisting of a) hydrogen, hydroxy, mercapto, cyano, nitro, alkyl of 1 to 4 carbon atoms unsubstituted or substituted by —OH, b) alkoxy of 1 to 4 carbon atoms unsubstituted or substituted with at least one fluorine, alkylthio of 1 to 6 carbon atoms, acyl of an organic carboxylic acid of 1 to 4 carbon atoms, amino and carbamoyl unsubstituted or substituted with a member selected from the group consisting of alkyl and alkenyl of up to 6 carbon atoms, free carboxy, salified carboxy, carboxy esterified with alkanol of 1 to 6 carbon atoms, A$_{1B}$ is nitrogen and A$_{2B}$ and A$_{3B}$ are

and R$_1$ is selected from the group consisting of hydrogen, hydroxyl, cyano, carboxy free, salified or esterified by alkyl of 1 to 4 carbon atoms, alkyl, alkenyl, alkoxy, acyl and alkylthio of up to 7 carbon atoms, phenyl, benzyl, phenoxy, phenylthio, all of the aliphatic or cyclic unsubstituted or substituted by a member of the group consisting of halogen, trifluoromethyl, cyano, carboxy free, salified or esterified by alkyl of 1 to 4 carbon atoms, tetrazole and isoxazole, and A$_{4B}$ is —C—R$_{5B}$—Y, R$_{5B}$ is —CH$_2$—, and Y is biphenyl unsubstituted or substituted by a member of the group consisting of hydroxyl, halogen, alkyl and alkoxy of 1 to 4 carbon atoms, trifluoromethyl, cyano nitro, free salified or esterified carboxy tetrazole and isoxazole and their non-toxic, pharmaceutically acceptable addition salts with mineral and organic acids and mineral and organic bases.

2. A compound of claim 1 which is 4'-[(2-butyl-4-quinolinyl)-methyl](1,1'-biphenyl)-2-carboxylic acid.

3. A compound of claim 1 wherein $R_1$ is selected from the group consisting of hydrogen, alkyl of 1 to 4 carbon atoms, free carboxy, salified carboxy and carboxy esterified with an alkanol of 1 to 6 carbon atoms.

4. A compound of claim 1 where $R_{2B}$ and $R_{3B}$ are individually hydrogen or alkylthio of 1 to 4 carbon atoms.

5. A compound of claim 1 where Y is biphenyl, unsubstituted or substituted by a member selected from the group consisting of hydroxyl, halogen, alkyl and alkoxy of 1 to 4 carbon atoms, trifuoromethyl, cyano, nitro, free, salified or esterified tetrazole and isoxazole.

6. A composition for inhibiting the effects of angiotensin II comprising an amount of at least one compound of claim 1 sufficient to inhibit angiotensin II effects and a pharmaceutical carrier.

7. A method of inhibiting the effects of angiotensin II in warm-blooded animals comprising administering to warm-blooded animals an amount of at least one compound of claim 1 sufficient to inhibit angiotensin II effects.

8. The method of claim 7 wherein the compound is 4'[(2-butyl-4-quinolinyl)-methyl](1,1'-biphenyl)-2-carboxylic acid.

* * * * *